US012778521B2

(12) United States Patent
Okumura

(10) Patent No.: US 12,778,521 B2
(45) Date of Patent: Nov. 3, 2026

(54) IMAGE PROCESSING DEVICE, IMAGE PROCESSING METHOD, AND IMAGE PROCESSING PROGRAM

(71) Applicant: FUJIFILM Corporation, Tokyo (JP)

(72) Inventor: Yukari Okumura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 494 days.

(21) Appl. No.: 18/151,820

(22) Filed: Jan. 9, 2023

(65) Prior Publication Data

US 2023/0146430 A1 May 11, 2023

Related U.S. Application Data

(63) Continuation of application No. PCT/JP2021/018613, filed on May 17, 2021.

(30) Foreign Application Priority Data

Jul. 22, 2020 (JP) ................................ 2020-125752

(51) Int. Cl.
*A61B 6/02* (2006.01)
*A61B 6/50* (2024.01)

(52) U.S. Cl.
CPC .............. *A61B 6/025* (2013.01); *A61B 6/502* (2013.01)

(58) Field of Classification Search
None
See application file for complete search history.

(56) References Cited

U.S. PATENT DOCUMENTS 7,760,924 B2 * 7/2010 Ruth ...................... G06T 15/08 382/128
8,983,156 B2 3/2015 Periaswamy et al.
(Continued)

FOREIGN PATENT DOCUMENTS

CA 3102174 C * 7/2022 ........... A61B 5/7267
CN 108074219 A * 5/2018 ............ A61B 6/527
(Continued)

OTHER PUBLICATIONS

Ravi K Samala et al.; "Computer-aided detection system for clustered microcalcifications in digital breast tomosynthesis using joint information from volumetric and planar projection images"; Physics in Medicine and Biology; Institute of Physics Publishing; Oct. 14, 2015; pp. 8457-8479; vol. 60, No. 21; Bristol, GB.
(Continued)

*Primary Examiner* — Ted W Barnes
(74) *Attorney, Agent, or Firm* — Studebaker Brackett PLLC

(57) ABSTRACT

A processor derives a linear structure image indicating a high-frequency linear structure from each of a plurality of tomographic images indicating tomographic planes of an object, derives a feature amount indicating features of the linear structure from the linear structure image, selects at least one tomographic image or high-frequency tomographic image including the linear structure or a predetermined tomographic image or high-frequency tomographic image on the basis of the feature amount for each corresponding pixel in each of the tomographic images or the high-frequency tomographic images indicating high-frequency components of the tomographic images, and derive a composite two-dimensional image on the basis of the selected tomographic images or high-frequency tomographic images.

12 Claims, 15 Drawing Sheets

(56) References Cited

U.S. PATENT DOCUMENTS

| | | | | |
|---|---|---|---|---|
| 9,792,703 | B2 * | 10/2017 | Costa | G06T 7/11 |
| 9,836,872 | B2 | 12/2017 | Erhard et al. | |
| 10,891,764 | B2 * | 1/2021 | Fukuda | G06T 11/008 |
| 2009/0041327 | A1 * | 2/2009 | Chen | G06T 7/0012 382/132 |
| 2010/0104155 | A1 * | 4/2010 | Chen | G06T 7/0012 382/128 |
| 2010/0246884 | A1 * | 9/2010 | Chen | G06T 7/0012 382/128 |
| 2011/0142323 | A1 * | 6/2011 | Chen | G06T 7/0012 382/132 |
| 2015/0052471 | A1 * | 2/2015 | Chen | A61B 6/025 715/771 |
| 2016/0140749 | A1 * | 5/2016 | Erhard | G06T 15/08 345/424 |
| 2016/0235380 | A1 * | 8/2016 | Smith | A61B 6/463 |
| 2017/0071554 | A1 * | 3/2017 | Fukuda | A61B 6/502 |
| 2017/0231593 | A1 * | 8/2017 | Fukuda | A61B 6/482 382/132 |
| 2017/0236276 | A1 * | 8/2017 | Fukuda | G06T 11/003 382/131 |
| 2018/0047211 | A1 | 2/2018 | Chen et al. | |
| 2018/0055459 | A1 * | 3/2018 | Fukuda | A61B 6/5205 |
| 2018/0185000 | A1 * | 7/2018 | Arai | G06T 11/008 |
| 2018/0292332 | A1 * | 10/2018 | Yamakawa | A61B 6/51 |
| 2018/0322633 | A1 * | 11/2018 | Kuratomi | G06T 7/74 |
| 2019/0392637 | A1 | 12/2019 | Chen et al. | |
| 2021/0049731 | A1 * | 2/2021 | Fukuda | G06T 1/0007 |
| 2021/0113167 | A1 * | 4/2021 | Chui | G06F 18/254 |
| 2022/0005277 | A1 | 1/2022 | Chen et al. | |
| 2022/0192615 | A1 | 6/2022 | Chui et al. | |

FOREIGN PATENT DOCUMENTS

| | | | | | |
|---|---|---|---|---|---|
| CN | 106023197 | B | * | 11/2018 | |
| EP | 3348195 | B1 | * | 7/2019 | A61B 6/025 |
| JP | 2004248817 | A | * | 9/2004 | G06T 7/0012 |
| JP | 2014-128716 | A | | 7/2014 | |
| JP | 2016-533803 | A | | 11/2016 | |
| JP | 2018-029746 | A | | 3/2018 | |
| JP | 2018-047256 | A | | 3/2018 | |
| JP | 6370280 | B2 | * | 8/2018 | A61B 6/02 |
| JP | 2020-512130 | A | | 4/2020 | |
| JP | 2020096752 | A | * | 6/2020 | |

OTHER PUBLICATIONS

The extended European search report issued by the European Patent Office on Dec. 22, 2023, which corresponds to European Patent Application No. 21846212.5-1224 and is related to U.S. Appl. No. 18/151,820.

An Office Action; "Notice of Reasons for Refusal," mailed by the Japanese Patent Office on Jan. 9, 2024, which corresponds to Japanese Patent Application No. 2022-538602 and is related to U.S. Appl. No. 18/151,820; with English language translation.

International Search Report issued in PCT/JP2021/018613; mailed Jul. 20, 2021.

International Preliminary Report On Patentability (Chapter I) and Written Opinion of the International Searching Authority issued in PCT/JP2021/018613; issued Jan. 24, 2023.

Office Action mailed by the Japanese Patent Office on May 14, 2024, which corresponds to Japanese Patent Application No. 2022-538602 and is related to U.S. Appl. No. 18/151,820; with English language translation.

* cited by examiner

IMAGE PROCESSING DEVICE, IMAGE PROCESSING METHOD, AND IMAGE PROCESSING PROGRAM

CROSS-REFERENCE TO RELATED APPLICATIONS

This application is a continuation application of International Application No. PCT/JP2021/018613 filed May 17, 2021 the disclosure of which is incorporated herein by reference in its entirety. Further, this application claims priorities from Japanese Patent Application No. 2020-125752, filed Jul. 22, 2020, the disclosure of which is incorporated herein by reference in their entirety.

TECHNICAL FIELD

The present disclosure relates to an image processing device, an image processing method, and an image processing program.

RELATED ART

In recent years, image diagnosis using a radiography apparatus (called mammography) for capturing an image of a breast has attracted attention in order to promote early detection of breast cancer. Further, in the mammography, tomosynthesis imaging has been proposed which moves a radiation source, irradiates the breast with radiation at a plurality of radiation source positions to acquire a plurality of projection images, and reconstructs the plurality of acquired projection images to generate tomographic images in which desired tomographic planes have been highlighted. In the tomosynthesis imaging, the radiation source is moved in parallel to a radiation detector or is moved so as to draw a circular or elliptical arc according to the characteristics of an imaging apparatus and the required tomographic image, and imaging is performed on the breast at a plurality of radiation source positions to acquire a plurality of projection images. Then, the projection images are reconstructed using, for example, a back projection method, such as a simple back projection method or a filtered back projection method, or a sequential reconstruction method to generate tomographic images.

The tomographic images are generated in a plurality of tomographic planes of the breast, which makes it possible to separate structures that overlap each other in a depth direction in which the tomographic planes are arranged in the breast. Therefore, it is possible to find an abnormal part such as a lesion that has been difficult to detect in a two-dimensional image (hereinafter, referred to as a simple two-dimensional image) acquired by simple imaging according to the related art which irradiates an object with radiation in a predetermined direction.

In addition, a technique has been known which combines a plurality of tomographic images having different distances (positions in a height direction) from a detection surface of a radiation detector to a radiation source, which have been acquired by tomosynthesis imaging, using, for example, an addition method, an averaging method, a maximum intensity projection method, or a minimum intensity projection method to generate a pseudo two-dimensional image (hereinafter, referred to as a composite two-dimensional image) corresponding to the simple two-dimensional image (see JP2014-128716A).

In contrast, in the medical field, a computer aided diagnosis (hereinafter, referred to as CAD) system has been known which automatically detects a structure, such as an abnormal shadow, in an image and displays the detected structure so as to be highlighted. For example, the CAD is used to detect important diagnostic structures, such as a tumor, a spicula, and a calcification, from the tomographic images acquired by the tomosynthesis imaging. In addition, a method has been proposed which, in a case in which a composite two-dimensional image is generated from a plurality of tomographic images acquired by performing the tomosynthesis imaging on the breast, detects a region of interest including a structure using the CAD and combines the detected region of interest on, for example, a projection image or a two-dimensional image acquired by simple imaging to generate a composite two-dimensional image (see the specification of U.S. Pat. No. 8,983,156B). Further, a method has been proposed which averages and combines tomographic images including only the structure detected by the CAD to generate a composite two-dimensional image (see the specification of U.S. Pat. No. 9,792,703B).

However, in the composite two-dimensional image generated by the method disclosed in the specification of U.S. Pat. No. 8,983,156B, the structure of interest combined with the two-dimensional image is only the structure of interest acquired from one tomographic image. Therefore, in a case in which linear structures including light and thin lines, such as a mammary gland structure and a spicula in the breast, is present across a plurality of tomographic images, it is not possible to reflect a state in which the structure is present in a depth direction in which the tomographic images are arranged in the composite two-dimensional image. In addition, the method disclosed in the specification of U.S. Pat. No. 9,792,703B averages the structures of interest included in a plurality of tomographic images. Therefore, for example, a fine structure of interest, such as a calcification, and a linear structure, such as a mammary gland or a spicula, included in the breast are faint and difficult to see.

SUMMARY

The present invention has been made in view of the above circumstances, and an object of the present invention is to make it easy to see a fine structure included in an object in a composite two-dimensional image.

According to the present disclosure, there is provided an image processing device comprising at least one processor. The processor is configured to derive a linear structure image indicating a high-frequency linear structure from each of a plurality of tomographic images indicating tomographic planes of an object, to derive a feature amount indicating features of the linear structure from the linear structure image, to select at least one tomographic image or high-frequency tomographic image including the linear structure or a predetermined tomographic image or high-frequency tomographic image on the basis of the feature amount for each corresponding pixel in each of the tomographic images or the high-frequency tomographic images indicating high-frequency components of the tomographic images, and to derive a composite two-dimensional image on the basis of the selected tomographic images or high-frequency tomographic images.

In addition, in the image processing device according to the present disclosure, the processor may be configured to select the at least one tomographic image or high-frequency tomographic image including the linear structure and to derive the composite two-dimensional image on the basis of a pre-composite image generated in advance on the basis of the tomographic images or the high-frequency tomographic images and the selected tomographic images or high-frequency tomographic images.

Further, in the image processing device according to the present disclosure, the processor may be configured to detect a predetermined structure of interest from the tomographic image or the high-frequency tomographic image, and to select the tomographic image or the high-frequency tomographic image from which the structure of interest has been detected, in a corresponding pixel in the tomographic images or the high-frequency tomographic images from which the structure of interest has been detected, instead of the tomographic image or the high-frequency tomographic image including the linear structure, or the predetermined tomographic image or high-frequency tomographic image.

In addition, in the image processing device according to the present disclosure, the object may be a breast, and the structure of interest may be a calcification.

Further, in the image processing device according to the present disclosure, the object may be a breast, and the linear structure may be a mammary gland and a spicula.

Furthermore, in the image processing device according to the present disclosure, the processor may be configured to derive a pixel value of the linear structure image as the feature amount.

In addition, in the image processing device according to the present disclosure, the processor may be configured to derive a variance value of each pixel of the linear structure image as the feature amount.

Further, in the image processing device according to the present disclosure, the processor may be configured to convert a pixel value of the linear structure image to derive the feature amount.

Furthermore, in the image processing device according to the present disclosure, the processor may be configured to select the tomographic image or the high-frequency tomographic image that includes the linear structure having at least a largest feature amount.

Moreover, in the image processing device according to the present disclosure, the processor may be configured to select the tomographic image or the high-frequency tomographic image that includes the linear structure having the feature amount equal to or greater than a predetermined threshold value.

In addition, according to the present disclosure, there is provided an image processing method comprising: deriving a linear structure image indicating a high-frequency linear structure from each of a plurality of tomographic images indicating tomographic planes of an object; deriving a feature amount indicating features of the linear structure from the linear structure image; selecting at least one tomographic image or high-frequency tomographic image including the linear structure or a predetermined tomographic image or high-frequency tomographic image on the basis of the feature amount for each corresponding pixel in each of the tomographic images or the high-frequency tomographic images indicating high-frequency components of the tomographic images; and deriving a composite two-dimensional image on the basis of the selected tomographic images or high-frequency tomographic images.

In addition, a program that causes a computer to perform the image processing method according to the present disclosure may be provided.

According to the present disclosure, it is possible to easily see a fine structure included in an object in a composite two-dimensional image.

DETAILED DESCRIPTION

Figure 1:
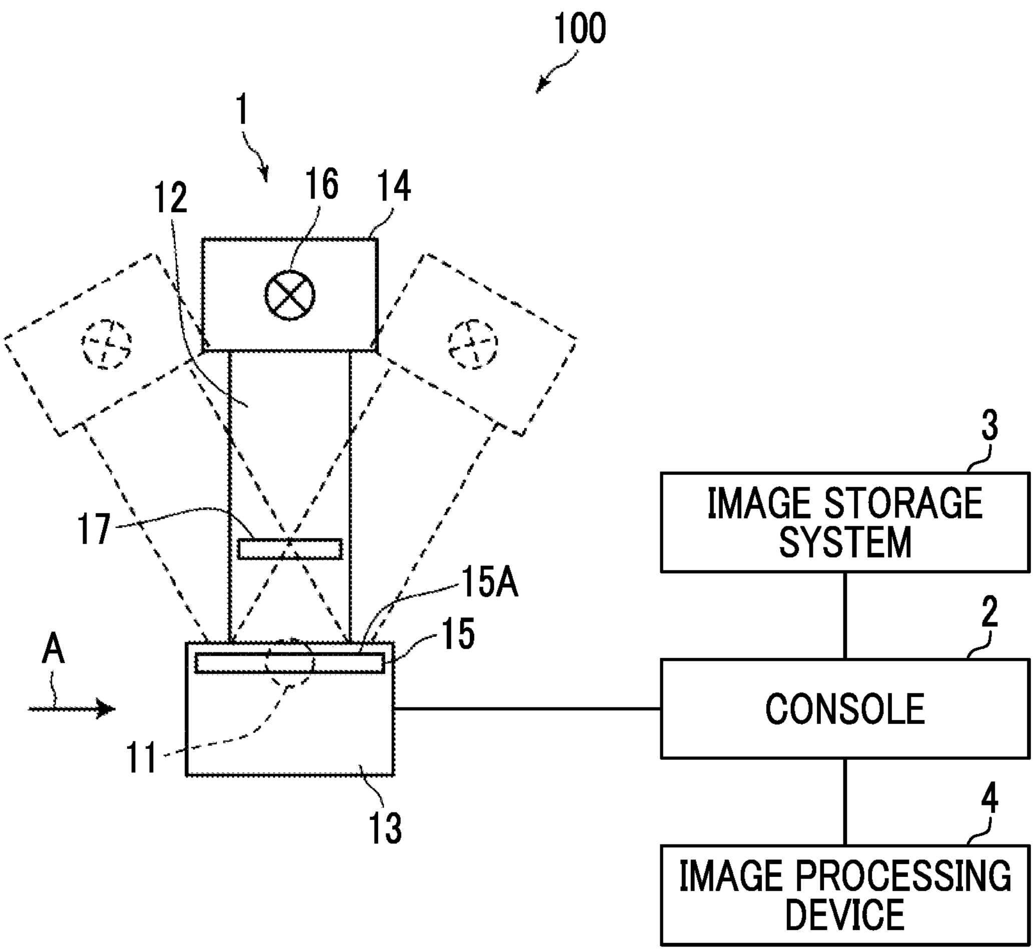
FIG. 1 is a diagram schematically illustrating a configuration of a radiography system to which an image processing device according to a first embodiment of the present disclosure is applied.
Figure 2:
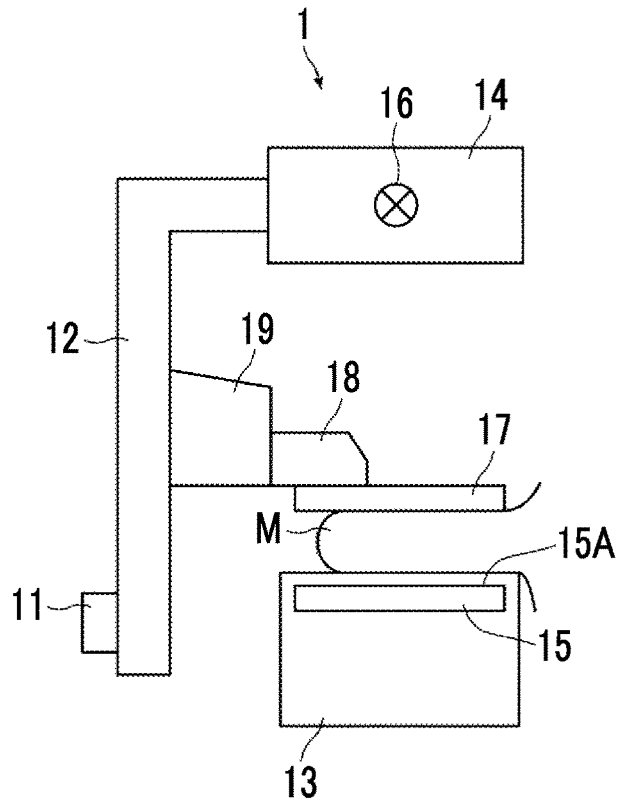
FIG. 2 is a diagram illustrating a radiography apparatus as viewed from a direction of an arrow A in FIG. 1.

Hereinafter, embodiments of the present disclosure will be described with reference to the drawings. FIG. 1 is a diagram schematically illustrating a configuration of a radiography system to which an image processing device according to an embodiment of the present disclosure is applied, and FIG. 2 is a diagram illustrating a mammography apparatus in the radiography system as viewed from a direction of an arrow A in FIG. 1. As illustrated in FIG. 1, a radiography system 100 according to this embodiment images a breast M, which is an object, at a plurality of radiation source positions and acquires a plurality of radiographic images, that is, a plurality of projection images, in order to perform tomosynthesis imaging on the breast to generate tomographic images. The radiography system 100 according to this embodiment comprises a mammography apparatus 1, a console 2, an image storage system 3, and an image processing device 4.

The mammography apparatus 1 comprises an arm portion 12 that is connected to a base (not illustrated) by a rotation shaft 11. An imaging table 13 is attached to one end of the arm portion 12, and a radiation emitting unit 14 is attached to the other end of the arm portion 12 so as to face the imaging table 13. The arm portion 12 is configured such that only the end to which the radiation emitting unit 14 is attached can be rotated. Therefore, the imaging table 13 is fixed, and only the radiation emitting unit 14 can be rotated.

A radiation detector 15, such as a flat panel detector, is provided in the imaging table 13. The radiation detector 15 has a detection surface 15A for radiation. In addition, for example, a circuit substrate including a charge amplifier that converts a charge signal read from the radiation detector 15 into a voltage signal, a correlated double sampling circuit that samples the voltage signal output from the charge amplifier, and an analog-digital (AD) conversion unit that converts the voltage signal into a digital signal is also provided in the imaging table 13.

A radiation source 16 is accommodated in the radiation emitting unit 14. The radiation source 16 emits, for example, X-rays as the radiation. The console 2 controls the timing when the radiation source 16 emits the radiation and the radiation generation conditions of the radiation source 16, that is, the selection of target and filter materials, a tube voltage, an irradiation time, and the like.

Further, the arm portion 12 is provided with a compression plate 17 that is disposed above the imaging table 13 and presses and compresses the breast M, a support portion 18 that supports the compression plate 17, and a movement mechanism 19 that moves the support portion 18 in an up-down direction in FIGS. 1 and 2. In addition, an interval between the compression plate 17 and the imaging table 13, that is, a compression thickness is input to the console 2.

The console 2 has a function of controlling the mammography apparatus 1 using, for example, an imaging order and various kinds of information acquired from a radiology information system (RIS) (not illustrated) or the like through a network, such as a wireless communication local area network (LAN), and instructions or the like directly issued by a radiology technician or the like. Specifically, the console 2 directs the mammography apparatus 1 to perform the tomosynthesis imaging on the breast M, acquires a plurality of projection images as described below, and reconstructs the plurality of projection images to generate a plurality of tomographic images. For example, in this embodiment, a server computer is used as the console 2.

The image storage system 3 is a system that stores image data such as radiographic images and tomographic images captured by the mammography apparatus 1. The image storage system 3 extracts an image corresponding to a request from, for example, the console 2 and the image processing device 4 from the stored images and transmits the image to a device that is the source of the request. A specific example of the image storage system 3 is a picture archiving and communication system (PACS).

Figure 3:
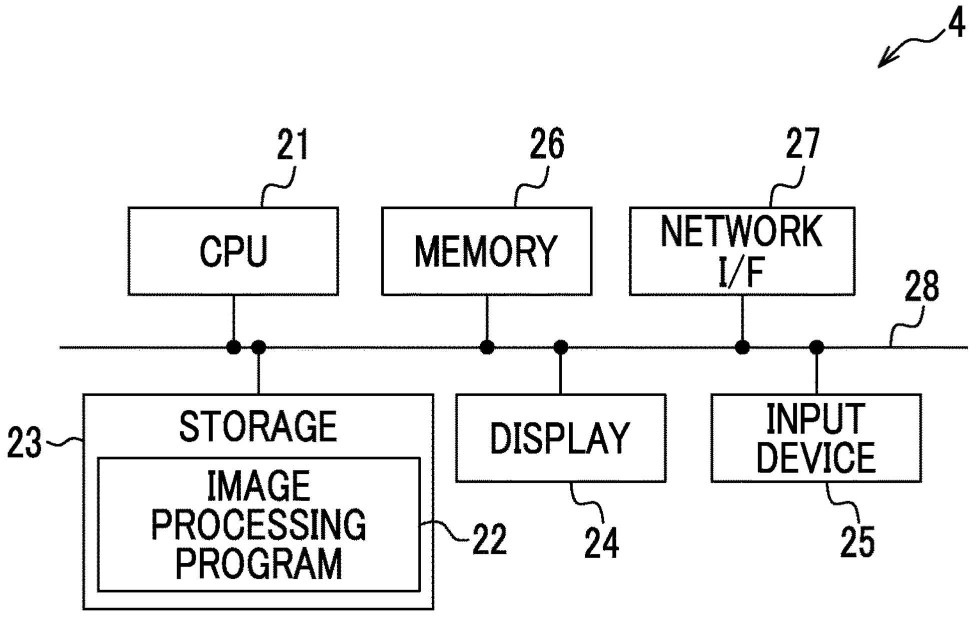
FIG. 3 is a diagram schematically illustrating a configuration of the image processing device according to a first embodiment.

Next, an image processing device according to a first embodiment will be described. Next, a hardware configuration of the image processing device according to the first embodiment will be described with reference to FIG. 3. As illustrated in FIG. 3, the image processing device 4 is a computer, such as a workstation, a server computer, or a personal computer, and comprises a central processing unit (CPU) 21, a non-volatile storage 23, and a memory 26 as a temporary storage area. In addition, the image processing device 4 comprises a display 24, such as a liquid crystal display, an input device 25, such as a keyboard and a mouse, and a network interface (I/F) 27 that is connected to a network (not illustrated). The CPU 21, the storage 23, the display 24, the input device 25, the memory 26, and the network I/F 27 are connected to a bus 28. In addition, the CPU 21 is an example of a processor according to the present disclosure.

The storage 23 is implemented by, for example, a hard disk drive (HDD), a solid state drive (SSD), and a flash memory. An image processing program 22 installed in the image processing device 4 is stored in the storage 23 as a storage medium. The CPU 21 reads out the image processing program 22 from the storage 23, expands the image processing program 22 in the memory 26, and executes the expanded image processing program 22.

In addition, the image processing program 22 is stored in a storage device of a server computer connected to the network or a network storage in a state in which it can be accessed from the outside and is downloaded and installed in the computer constituting the image processing device 4 as required. Alternatively, the programs are recorded on a recording medium, such as a digital versatile disc (DVD) or a compact disc read only memory (CD-ROM), are distributed, and are installed in the computer constituting the image processing device 4 from the recording medium.

Figure 4:
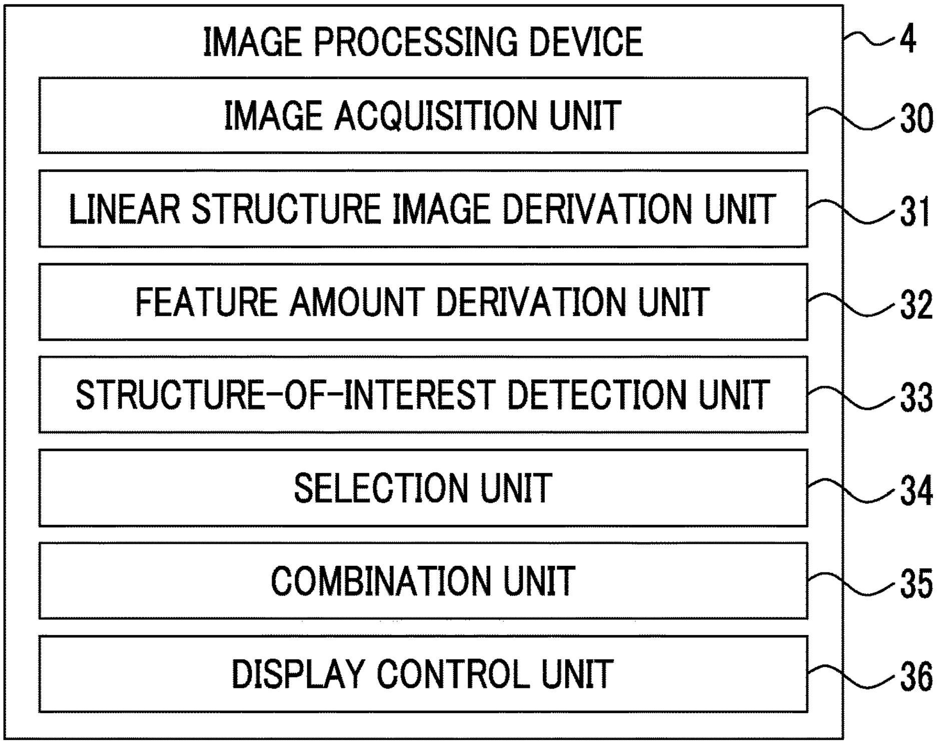
FIG. 4 is a diagram illustrating a functional configuration of the image processing device according to the first embodiment.

Next, a functional configuration of the image processing device according to the first embodiment will be described. FIG. 4 is a diagram illustrating the functional configuration of the image processing device according to the first embodiment. As illustrated in FIG. 4, the image processing device 4 comprises an image acquisition unit 30, a linear structure image derivation unit 31, a feature amount derivation unit 32, a structure-of-interest detection unit 33, a selection unit 34, a combination unit 35, and a display control unit 36. Then, the CPU 21 executes the image processing program 22 such that the image processing device 4 functions as the image acquisition unit 30, the linear structure image derivation unit 31, the feature amount derivation unit 32, the structure-of-interest detection unit 33, the selection unit 34, the combination unit 35, and the display control unit 36.

The image acquisition unit 30 acquires the tomographic image from the console 2 or the image storage system 3 through the network I/F 27.

Here, the tomosynthesis imaging and the generation of tomographic images in the console 2 will be described. In a case in which the tomosynthesis imaging for generating tomographic images is performed, the console 2 rotates the arm portion 12 about the rotation shaft 11 to move the radiation source 16, irradiates the breast M, which is an object, with radiation at a plurality of radiation source positions caused by the movement of the radiation source 16 under predetermined imaging conditions for tomosynthesis imaging, detects the radiation transmitted through the breast M using the radiation detector 15, and acquires a plurality of projection images Gi (i=1 to n, where n is the number of radiation source positions and is, for example, 15) at the plurality of radiation source positions.

Figure 5:
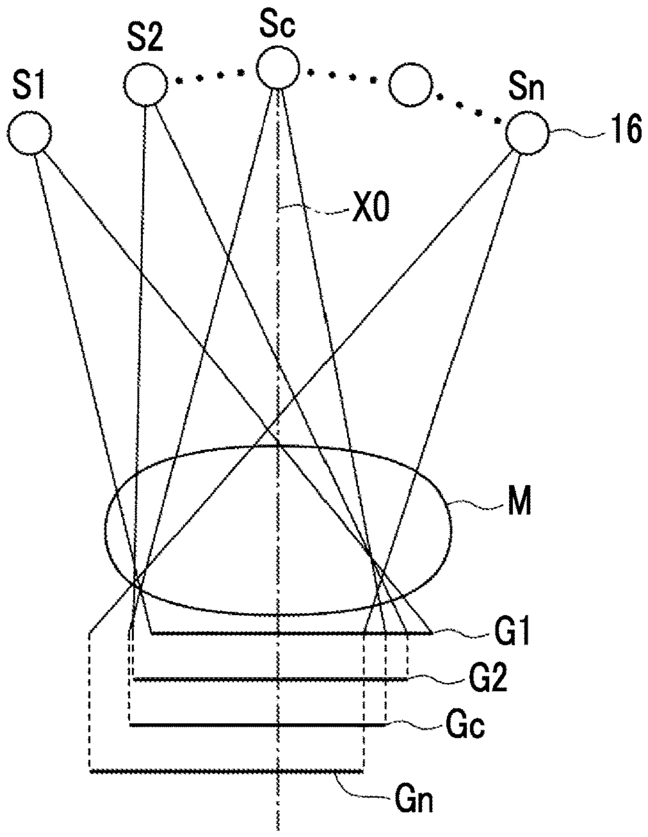
FIG. 5 is a diagram illustrating the acquisition of projection images.

FIG. 5 is a diagram illustrating the acquisition of the projection images Gi. As illustrated in FIG. 5, the radiation source 16 is moved to each of radiation source positions S1, S2, . . . , and Sn. The radiation source 16 is driven at each radiation source position to irradiate the breast M with radiation. The radiation detector 15 detects the radiation transmitted through the breast M to acquire projection images G1, G2, . . . , and Gn corresponding to the radiation source positions S1 to Sn, respectively. In addition, at each of the radiation source positions S1 to Sn, the breast M is irradiated with the same dose of radiation.

Furthermore, in FIG. 5, a radiation source position Sc is a radiation source position where an optical axis X0 of the radiation emitted from the radiation source 16 is orthogonal to the detection surface 15A of the radiation detector 15. It is assumed that the radiation source position Sc is referred to as a reference radiation source position Sc.

Figure 6:
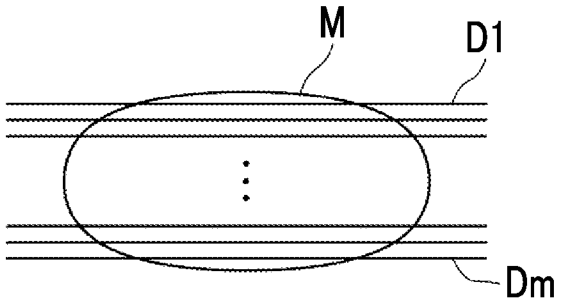
FIG. 6 is a diagram illustrating the generation of tomographic images.

Then, the console 2 reconstructs the plurality of projection images Gi to generate tomographic images in which the desired tomographic planes of the breast M have been highlighted. Specifically, the console 2 reconstructs the plurality of projection images Gi using a known back projection method, such as a simple back projection method or a filtered back projection method, to generate a plurality of tomographic images Dj (j=1 to m) in each of a plurality of tomographic planes of the breast M as illustrated in FIG. 6. In this case, a three-dimensional coordinate position in a three-dimensional space including the breast M is set, the pixel values of the corresponding pixels in the plurality of projection images Gi are reconstructed for the set three-dimensional coordinate position, and pixel values at the coordinate positions of the pixels are calculated. In addition, in the first embodiment, it is assumed that the pixel values of the tomographic images Dj become larger as brightness becomes higher (that is, closer to white) and become smaller as the brightness becomes lower (that is, closer to black). Further, it is assumed that the pixel value is equal to or greater than 0.

The console 2 directly transmits the generated tomographic images Dj to the image processing device 4 or transmits the generated tomographic images Dj to the image storage system 3.

The linear structure image derivation unit 31 derives a linear structure image indicating a high-frequency linear structure from each of a plurality of tomographic images Dj. The high-frequency linear structure in this embodiment is a linear structure with a thickness that is not capable of being clearly expressed in a composite two-dimensional image by the methods disclosed in, for example, U.S. Pat. Nos. 8,983,156B and 9,792,703B. Specifically, the high-frequency linear structure is a linear structure having a thickness of about 200 to 300 μm or less in the structures included in the breast M. Examples of the high-frequency linear structure include a mammary gland and a spicula included in the breast M.

Meanwhile, an example of the lesion included in the breast M is a tumor. The tumor has a larger structure than the calcification and the spicula. A structure, such as a tumor, having a larger structure than the calcification and the spicula is referred to as a low-frequency structure in this embodiment.

Figure 7:
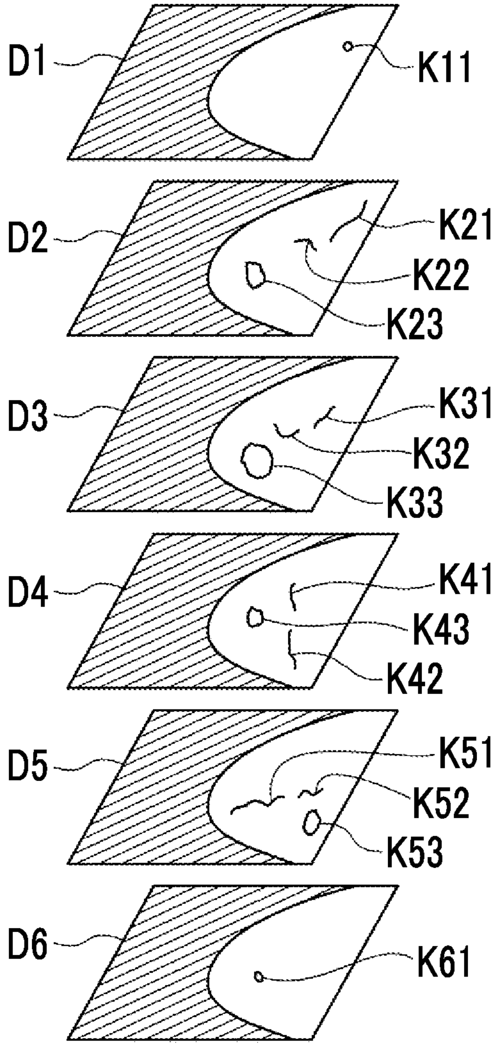
FIG. 7 is a diagram illustrating an example of the tomographic images.

FIG. 7 is a diagram illustrating an example of the tomographic images. In addition, FIG. 7 illustrates six tomographic images D1 to D6. As illustrated in FIG. 7, the tomographic image D1 includes a calcification K11. The tomographic image D2 includes linear structures K21 and K22 and a low-frequency structure K23 such as a tumor. The tomographic image D3 includes linear structures K31 and K32 and a low-frequency structure K33. The tomographic image D4 includes linear structures K41 and K42 and a low-frequency structure K43. The tomographic image D5 includes linear structures K51 and K52 and a low-frequency structure K53. The tomographic image D6 includes a calcification K61. In addition, FIG. 7 schematically illustrates various structures included in the breast M in the tomographic images Dj and is different from the actual inclusion of the structures.

First, the linear structure image derivation unit 31 derives high-frequency components in each of the plurality of tomographic images Dj in order to derive the linear structure image. Specifically, each of the tomographic images Dj is reduced to derive low-frequency tomographic images DLj indicating low-frequency components of the tomographic images Dj. Then, the low-frequency tomographic images DLj are enlarged to the same size as the original tomographic images Dj, and the enlarged low-frequency tomographic images DLj are subtracted from the original tomographic images Dj to derive high-frequency tomographic images DHj indicating high-frequency components of the tomographic images Dj. In addition, a filtering process using a low-pass filter may be performed on the tomographic image Dj to derive the low-frequency tomographic image DLj, instead of reducing the tomographic image Dj. Further, a filtering process using a high-pass filter may be performed on the tomographic images Dj to derive the high-frequency tomographic images DHj indicating the high-frequency components of the tomographic images Dj. Furthermore, a filtering process using a bandpass filter which extracts a high-frequency component having a thickness of about 300 μm or less in the tomographic image Dj may be performed to derive the high-frequency tomographic image DHj indicating the high-frequency component of the tomographic image Dj.

Figure 8:
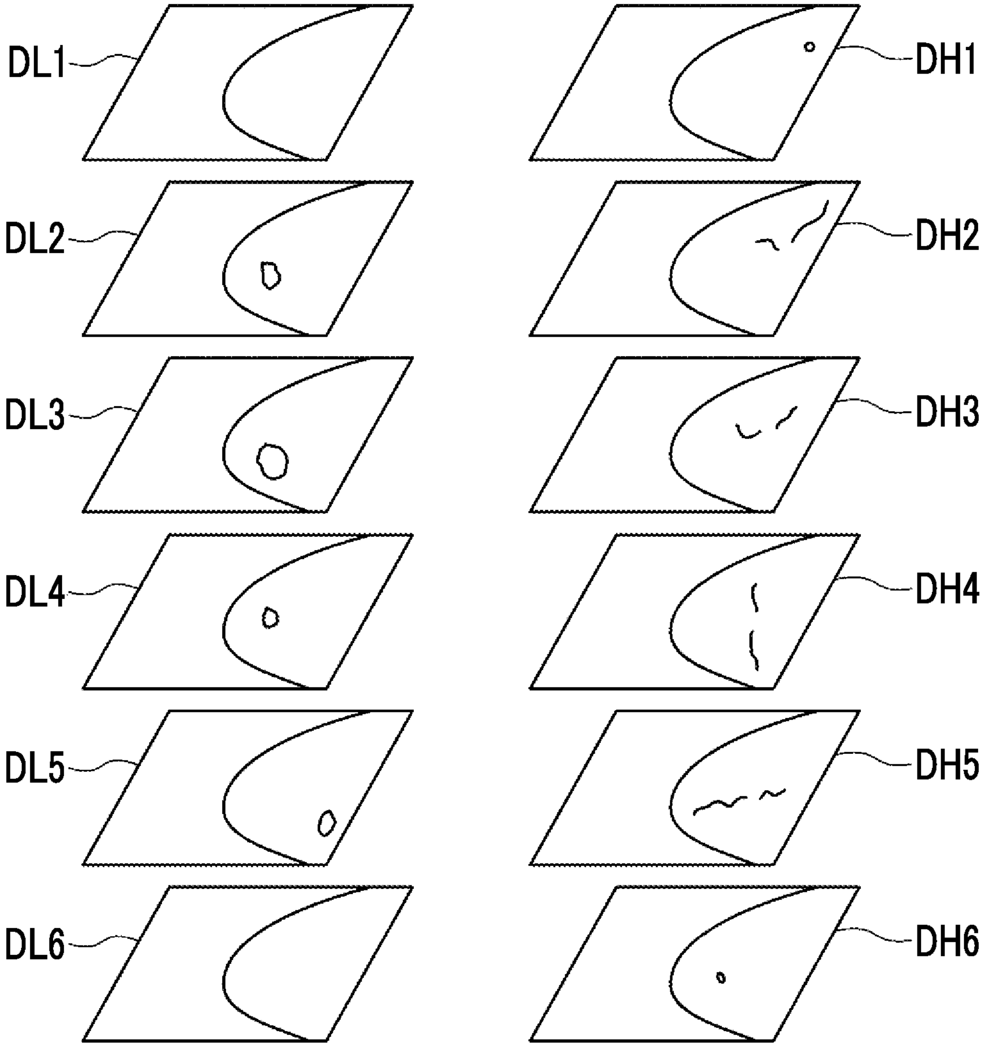
FIG. 8 is a diagram illustrating low-frequency tomographic images and high-frequency tomographic images.

FIG. 8 is a diagram illustrating low-frequency tomographic images and high-frequency tomographic images. In addition, FIG. 8 illustrates low-frequency tomographic images DL1 to DL6 and high-frequency tomographic images DH1 to DH6 derived from the tomographic images D1 to D6 illustrated in FIG. 7. As illustrated in FIG. 8, the low-frequency tomographic images DL1 to DL6 include only low-frequency structures having a relatively large size such as tumors included in the tomographic images D1 to D6. The high-frequency tomographic images DH1 to DH6 include only high-frequency structures having a relatively small size such as a spicula, a mammary gland, and a calcification.

In addition, in the low-frequency tomographic images DLj, the low-frequency structure is represented to have high brightness (that is, a large pixel value). Further, in the high-frequency tomographic images DHj, the high-frequency structure is represented to have high brightness.

Then, the linear structure image derivation unit 31 applies a directional filter in a direction, in which the pixels of the high-frequency tomographic images DHj are connected, to extract the high-frequency linear structures and derives high-frequency linear structure images DSj. Here, the directional filter is a two-dimensional filter, has a large weight for each of a vertical direction, a horizontal direction, and two diagonal directions in the filter, and smooths the image in other portions. The directional filters are prepared for each of the vertical direction, the horizontal direction, and the two diagonal directions.

Figure 9:
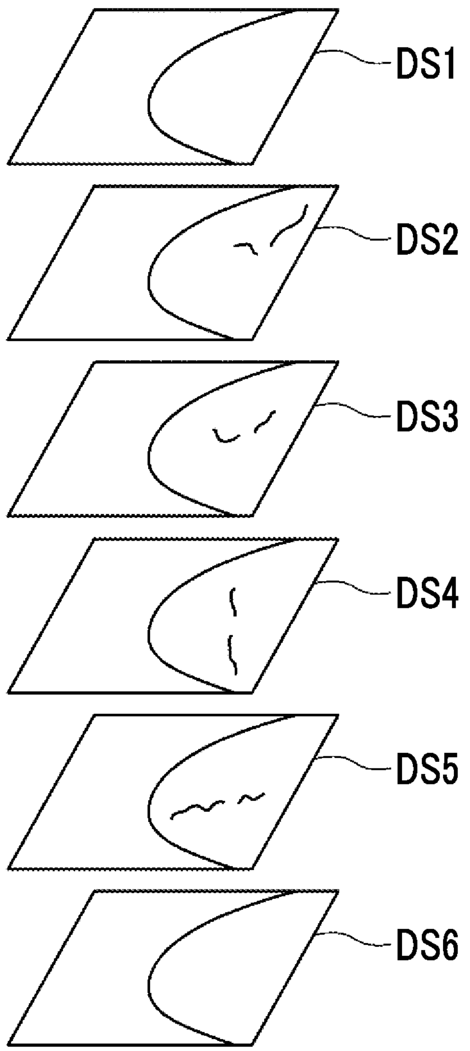
FIG. 9 is a diagram illustrating linear structure images.

FIG. 9 is a diagram illustrating linear structure images. In addition, FIG. 9 illustrates linear structure images DS1 to DS6 derived from the high-frequency tomographic images DH1 to DH6 illustrated in FIG. 8. As illustrated in FIG. 9, the linear structure images DS1 to DS6 include only linear structures, such as a mammary gland and a spicula, included in the tomographic images Dj. Further, in the linear structure images DSj, linear structures, such as the mammary gland and the spicula, included in the tomographic images Dj are represented to have high brightness (that is, a large pixel value).

The linear structure image derivation unit 31 may perform a filtering process using a Sobel filter, a Laplacian filter, or the like on the tomographic images Dj to derive the linear structure images DSj. In addition, the linear structure images DSj may be derived by extracting the linear structures from the tomographic images Dj using CAD.

The feature amount derivation unit 32 derives a feature amount indicating the features of the linear structure from the linear structure images DSj. In the first embodiment, a variance value of the pixel value of each pixel in the linear structure images DSj is derived as the feature amount. Specifically, the feature amount derivation unit 32 sets a region of interest with a predetermined size for each pixel of the linear structure images DSj. The size of the region of interest can be, for example, 5×5 pixels. However, the present disclosure is not limited thereto. The region of interest may have any size such as 3×3 pixels or 7×7 pixels. Further, the shape of the region of interest is not limited to a rectangular shape and may be any shape such as a circular shape.

The feature amount derivation unit 32 derives a variance value $\sigma^2$ of each pixel of the linear structure images DSj as the feature amount indicating the features of the linear structure on the basis of the pixel values of the pixels in the region of interest using the following Expression (1). In Expression (1), r(xi, yi) is the pixel value of each pixel of the linear structure images DSj, rm is an average value of the pixel values in the region of interest, and Σ is the sum of $(r(xi, yi)-rm)^2$ in the region of interest.

$$\sigma^2(x,y)=\Sigma(r(xi,yi)-rm)^2 \quad (1)$$

The structure-of-interest detection unit 33 detects the calcification from each of the tomographic images Dj or the high-frequency tomographic images DHj. The calcification is an example of a structure of interest according to the present disclosure. The structure-of-interest detection unit 33 sets the region of interest with a predetermined size for each pixel in order to detect the calcification. The size of the region of interest can be, for example, 5×5 pixels. However, the present disclosure is not limited thereto. The region of interest may have any size such as 3×3 pixels or 7×7 pixels. Further, the shape of the region of interest is not limited to a rectangular shape and may be any shape such as a circular shape. In addition, in the following description, the detection of the calcification from the tomographic images Dj will be described. However, the calcification can also be detected from the high-frequency tomographic images DHj as in the case of the tomographic images Dj.

The structure-of-interest detection unit 33 derives a variance value $\sigma 1^2$ of each pixel of the tomographic images Dj on the basis of the pixel values of the pixels in the region of interest using the following Expression (2). In Expression (2), r1(x1i, y1i) is the pixel value of each pixel of the tomographic images Dj, r1m is an average value of the pixel values in the region of interest, and Σ is the sum of $(r1(x1i, y1i)-r1m)^2$ in the region of interest.

$$\sigma 1^2(x,y)=\Sigma(r1(x1i,y1i)-r1m)^2 \quad (2)$$

The structure-of-interest detection unit 33 detects a pixel having a variance value $\sigma 1^2$ equal to or greater than a predetermined threshold value Th1 as a pixel of the calcification in the tomographic images Dj. In addition, the detection of the calcification is not limited to the method using the variance value. The pixel of the calcification may be detected by a filtering process using a filter that can extract a pixel having a brightness equal to or greater than a predetermined threshold value Th2. Further, the pixel of the calcification may be detected from the tomographic images Dj by CAD.

The selection unit 34 selects the high-frequency tomographic images DHj used to generate a composite two-dimensional image, which will be described below, for each corresponding pixel in each of the high-frequency tomographic images DHj on the basis of the feature amounts derived by the feature amount derivation unit 32 and the calcification detected by the structure-of-interest detection unit 33. In the first embodiment, at least one high-frequency tomographic image including the linear structure or a predetermined high-frequency tomographic image is selected for each corresponding pixel in each of the high-frequency tomographic images DHj. In particular, in the first embodiment, among the high-frequency tomographic images DHj, a maximum of three high-frequency tomographic images having a large feature amount in the linear structure images DSj are selected as the high-frequency tomographic images including the linear structure for each corresponding pixel in the high-frequency tomographic images DHj. Specifically, the selection unit 34 compares the feature amounts of the pixels corresponding to the pixel of interest in the linear structure images DSj for the corresponding pixel of interest in the high-frequency tomographic images DHj. Then, the selection unit 34 specifies a maximum of three linear structure images DSj having a large feature amount.

For example, in a case in which the feature amounts of the corresponding pixel of interest in the six linear structure images DS1 to DS6 are 10, 30, 10, 40, 20, and 50, respectively, the selection unit 34 specifies the linear structure images DS2, DS4, and DS6 as the linear structure images having a large feature amount for the pixel of interest. Then, the selection unit 34 selects the high-frequency tomographic images DH2, DH4, and DH6 corresponding to the specified linear structure images DS2, DS4, and DS6 as the high-frequency tomographic images DHj including the linear structure for the pixel of interest. In addition, a maximum of three high-frequency tomographic images DHj having a feature amount equal to or greater than a predetermined threshold value Th3 may be selected as the high-frequency tomographic images including the linear structure.

In addition, the number of selected high-frequency tomographic images DHj including the linear structure is not limited to a maximum of three. For example, for each corresponding pixel in the high-frequency tomographic images DHj, only one high-frequency tomographic image having the maximum feature amount in the linear structure images DSj may be selected as the high-frequency tomographic image including the linear structure. In addition, all of the high-frequency tomographic images having a feature amount equal to or greater than a predetermined threshold value Th4 in the linear structure images DSj may be selected as the high-frequency tomographic images including the linear structure. Further, in a case in which the number of high-frequency tomographic images having a feature amount greater than 0 among the six high-frequency tomographic images DH1 to DH6 is less than three, the selection unit 34 may select one or two high-frequency tomographic images having a feature amount greater than 0 as the high-frequency tomographic images including the linear structure.

In addition, in a case in which all of the high-frequency tomographic images DHj have a feature amount of 0 in the linear structure images DSj in the corresponding pixel in the high-frequency tomographic images DHj, the selection unit 34 selects all of the high-frequency tomographic images DHj as the predetermined high-frequency tomographic images for the pixel. Further, for the corresponding pixels in the high-frequency tomographic images DHj, the high-frequency tomographic image DHj having the maximum pixel value (that is, the maximum brightness) may be selected as the predetermined high-frequency tomographic image. Furthermore, a predetermined number (for example, a maximum of three) of high-frequency tomographic images DHj in descending order of the pixel value in the corresponding pixel in the high-frequency tomographic images DHj may be selected as the predetermined high-frequency tomographic images.

Meanwhile, in the first embodiment, in a case in which the calcification is detected in the corresponding pixel in the high-frequency tomographic images DHj, the selection unit 34 selects the high-frequency tomographic image in which the calcification has been detected, regardless of the magnitude of the feature amount of the linear structure derived by the feature amount derivation unit 32. For example, it is assumed that the calcification is detected in the pixel of interest in the high-frequency tomographic images DHj. In this case, even in a case in which the high-frequency tomographic image including the linear structure is selected for the pixel of interest, the high-frequency tomographic image in which the calcification has been detected is selected instead of the high-frequency tomographic image including the linear structure. In addition, in a case in which the predetermined high-frequency tomographic images are selected for the pixel of interest and the calcification is detected in at least one of the high-frequency tomographic images, the selection unit 34 selects the high-frequency tomographic image in which the calcification has been detected, instead of the predetermined high-frequency tomographic images.

Further, in a case in which the number of high-frequency tomographic images in which the calcification has been detected in the pixel of interest is three or more, the selection unit 34 may select a maximum of three high-frequency tomographic images corresponding to the tomographic images in which the calcification has been detected, instead of the three high-frequency tomographic images including the linear structure. In this case, the selection unit 34 selects the top three high-frequency tomographic images having a large variance value at the time of detecting the calcification.

Furthermore, in a case in which the number of high-frequency tomographic images in which the calcification has been detected in the pixel of interest is equal to or less than two, the selection unit 34 may select two or one high-frequency tomographic image in which the calcification has been detected, instead of two or one of the high-frequency tomographic image including the linear structure. In this case, one or two high-frequency tomographic images including the linear structure may be left as they are.

For example, it is assumed that three high-frequency tomographic images DH1, DH2, and DH3 including the linear structure are selected in the pixel of interest. It is assumed that the magnitudes of the feature amounts of the linear structures satisfy DH1>DH2>DH3. Further, it is assumed that the calcification is detected in the high-frequency tomographic image DH4 for the pixel of interest. In this case, the selection unit 34 selects the high-frequency tomographic image DH4 in the pixel of interest, instead of the high-frequency tomographic image DH1 having the minimum feature amount among the high-frequency tomographic images DH1, DH2, and DH3 including the linear structure. Further, it is assumed that the calcification is detected in the high-frequency tomographic images DH4, DH5, and DH6 in the pixel of interest. In this case, the selection unit 34 selects the high-frequency tomographic images DH4, DH5, and DH6 in the pixel of interest, instead of the high-frequency tomographic images DH1, DH2, and DH3 including the linear structure.

Figure 10:
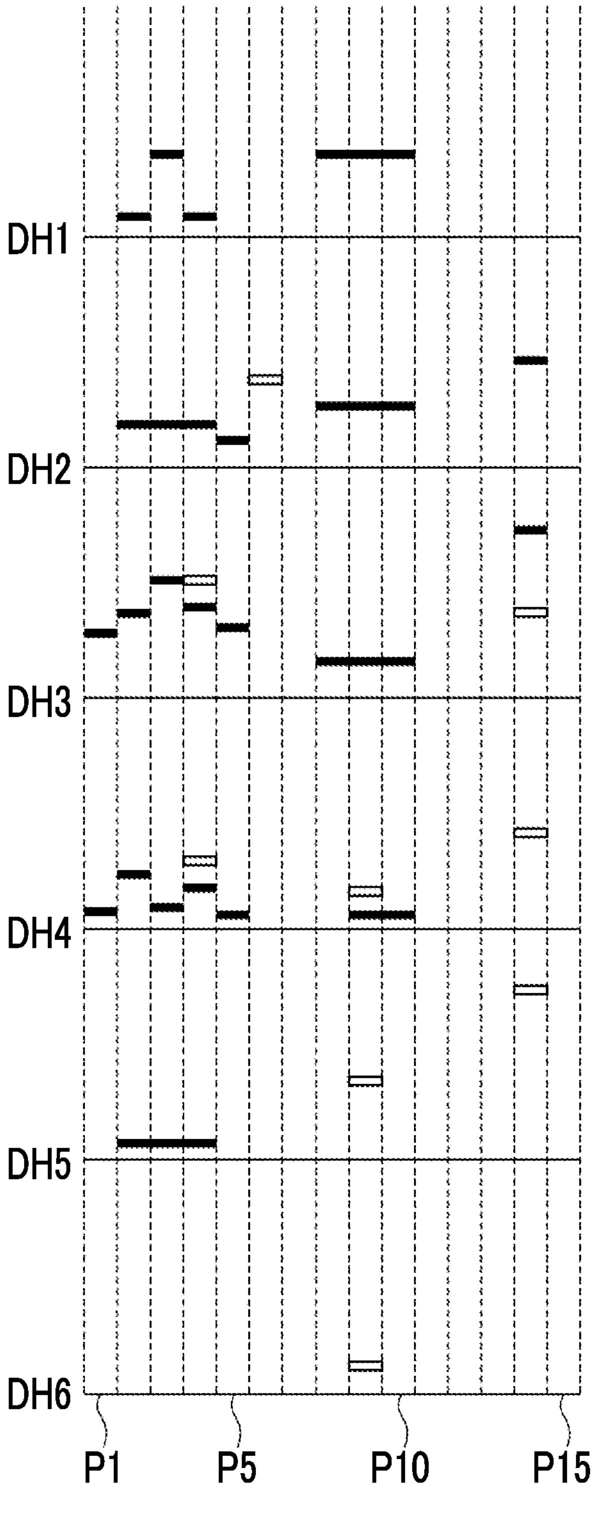
FIG. 10 is a diagram illustrating the selection of the high-frequency tomographic image in the first embodiment.

FIG. 10 is a diagram illustrating the selection of the high-frequency tomographic image based on the feature amount and the calcification. In addition, in FIG. 10, the selection of the high-frequency tomographic images from the six high-frequency tomographic images DH1 to DH6 illustrated in FIG. 8 will be described. Further, in FIG. 10, the high-frequency tomographic images DH1 to DH6 are schematically illustrated one-dimensionally. The high-frequency tomographic images DH1 to DH6 have 15 pixels P1 to P15. Furthermore, in FIG. 10, reference numerals are given only to the pixels P1, P5, P10, and P15 of the high-frequency tomographic image DH6. In addition, in FIG. 10, the feature amounts and the variance values of the calcifications derived from the linear structure images DS1 to DS6 are illustrated in each pixel of the high-frequency tomographic images DH1 to DH6.

In FIG. 10, the feature amount of the linear structure is represented by a thick line, and the variance value of the calcification is represented by a thick white line. In addition, as the distance from the schematically illustrated high-frequency tomographic images DH1 to DH6 to the upper side becomes longer, the value of the feature amount of the linear structure becomes larger, and the variance value at the time of detecting the calcification becomes larger. In addition, here, in the following description, it is assumed that a maximum of three high-frequency tomographic images DHj including the linear structure having a feature amount equal to or greater than the threshold value are selected. Therefore, FIG. 10 illustrates only the feature amounts of the linear structures which are equal to or greater than the threshold value. Furthermore, in the following description, the same figures as FIG. 10 are illustrated in the same manner as FIG. 10.

In the pixel P1, the feature amount of the linear structure is derived in the high-frequency tomographic images DH3 and DH4. In this case, the selection unit 34 selects the two high-frequency tomographic images DH3 and DH4 including the linear structure in the pixel P1.

In the pixel P2, the feature amount of the linear structure is derived in the high-frequency tomographic images DH1 to DH5. Among the high-frequency tomographic images DH1 to DH5, the high-frequency tomographic images having the top three feature amounts are the high-frequency tomographic images DH2 to DH4. Therefore, the selection unit 34 selects the three high-frequency tomographic images DH2 to DH4 including the linear structure in the pixel P2.

In the pixel P3, the feature amount of the linear structure is derived in the high-frequency tomographic images DH1 to DH5. Among the high-frequency tomographic images DH1 to DH5, the high-frequency tomographic images having the top three feature amounts are the high-frequency tomographic images DH1 to DH3. Therefore, the selection unit 34 selects the three high-frequency tomographic images DH1 to DH3 including the linear structure in the pixel P3.

In the pixel P4, the feature amount of the linear structure is derived in the high-frequency tomographic images DH1 to DH5. Among the high-frequency tomographic images DH1 to DH5, the high-frequency tomographic images having the top three feature amounts are the high-frequency tomographic images DH2 to DH4. In addition, in the pixel P4, the calcification is detected in two high-frequency tomographic images DH3 and DH4. Therefore, first, the selection unit 34 selects the two high-frequency tomographic images DH3 and DH4, in which the calcification has been detected, in the pixel P4. In addition, the selection unit 34 selects one high-frequency tomographic image DH2 including the linear structure excluding the high-frequency tomographic images DH3 and DH4, which have already been selected, among the high-frequency tomographic images DH2 to DH4 having the top three feature amounts. Further, the selection unit 34 may select only the high-frequency tomographic images DH3 and DH4, in which the calcification has been detected, in the pixel P4.

In the pixel P5, the feature amount of the linear structure is derived in three high-frequency tomographic images DH2 to DH4. Therefore, the selection unit 34 selects the three high-frequency tomographic images DH2 to DH4 including the linear structure in the pixel P5.

In the pixel P6, the feature amount of the linear structure is not derived in any of the high-frequency tomographic images DH1 to DH6. In addition, in the pixel P6, the calcification is detected in the high-frequency tomographic image DH2. Therefore, the selection unit 34 selects only the high-frequency tomographic image DH2, in which the calcification has been detected, in the pixel P6.

In the pixel P7, the feature amount of the linear structure is not derived in any of the high-frequency tomographic images DH1 to DH6. In addition, the calcification is not detected. Therefore, the selection unit 34 selects all of the high-frequency tomographic images DH1 to DH6 as the predetermined high-frequency tomographic images in the pixel P7.

In the pixel P8, the feature amount of the linear structure is derived in three high-frequency tomographic images DH1 to DH3. Therefore, the selection unit 34 selects the three high-frequency tomographic images DH1 to DH3 including the linear structure in the pixel P8.

In the pixel P9, the feature amount of the linear structure is derived in the high-frequency tomographic images DH1 to DH4. Among the high-frequency tomographic images DH1 to DH4, the high-frequency tomographic images having the top three feature amounts are the high-frequency tomographic images DH1 to DH3. Meanwhile, in the pixel P9, the calcification is detected in three high-frequency tomographic images DH4 to DH6. Therefore, the selection unit 34 selects the three high-frequency tomographic images DH4 to DH6, in which the calcification has been detected, in the pixel P9.

In the pixel P10, the feature amount of the linear structure is derived in the high-frequency tomographic images DH1 to DH4. Among the high-frequency tomographic images DH1 to DH4, the high-frequency tomographic images having the top three feature amounts are the high-frequency tomographic images DH1 to DH3. Therefore, the selection unit 34 selects the three high-frequency tomographic images DH1 to DH3 including the linear structure in the pixel P10.

In the pixels P11 to P13, the feature amount of the linear structure is not derived in any of the high-frequency tomographic images DH1 to DH6. In addition, the calcification is not detected. Therefore, the selection unit 34 selects all of the high-frequency tomographic images DH1 to DH6 as the predetermined high-frequency tomographic images in the pixels P11 to P13.

In the pixel P14, the feature amount of the linear structure is derived in the high-frequency tomographic images DH2 and DH4. Meanwhile, in the pixel P14, the calcification is detected in the three high-frequency tomographic images DH3 and DH5. Therefore, the selection unit 34 selects the three high-frequency tomographic images DH3 to DH5, in which the calcification has been detected, in the pixel P14.

In the pixel P15, the feature amount of the linear structure is not derived in any of the high-frequency tomographic images DH1 to DH6. In addition, the calcification is not detected. Therefore, the selection unit 34 selects all of the high-frequency tomographic images DH1 to DH6 as the predetermined high-frequency tomographic images in the pixel P15.

The combination unit 35 derives a composite two-dimensional image on the basis of the high-frequency tomographic images selected by the selection unit 34. That is, in a region of the linear structure and a region of the calcification, the combination unit 35 derives the composite two-dimensional image on the basis of the high-frequency tomographic images including the linear structure and the high-frequency tomographic images in which the calcification has been detected. In addition, in a region other than the linear structure and the calcification, a composite two-dimensional image is derived on the basis of the predetermined high-frequency tomographic images.

Here, in the first embodiment, the combination unit 35 derives a composite high-frequency image GH1 which is a composite two-dimensional image for the high-frequency tomographic images DHj on the basis of the selected high-frequency tomographic images. In addition, the combination unit 35 derives a composite low-frequency image GL1 which is a composite two-dimensional image for the low-frequency tomographic images DLj indicating low-frequency components of the tomographic images Dj used in a case in which the linear structure image derivation unit 31 derives the linear structure images DSj. Then, the combination unit 35 derives a composite two-dimensional image CG1 from the composite high-frequency image GH1 and the composite low-frequency image GL1.

First, the derivation of the composite high-frequency image GH1 will be described. In addition, in the first embodiment, it is assumed that the high-frequency tomographic images are selected as described above with reference to FIG. 10. Therefore, combination for each of the pixels P1 to P15 will be described below.

In the pixel P1, two high-frequency tomographic images DH3 and DH4 including the linear structure are selected. Therefore, the combination unit 35 derives a weighted average value of the pixel values of the pixels P1 in the high-frequency tomographic images DH3 and DH4 according to the feature amounts (that is, the variance values) and sets the weighted average value as the pixel value of the pixel P1 in the composite high-frequency image GH1. In addition, a weighting coefficient for the weighted average is derived such that it becomes larger as the feature amount becomes larger. In addition, an added average value may be used instead of the weighted average value. This holds for the following description.

In the pixel P2, three high-frequency tomographic images DH2 to DH4 including the linear structure are selected. Therefore, the combination unit 35 derives a weighted average value of the pixel values of the pixels P2 in the high-frequency tomographic images DH2 to DH4 according to the feature amounts and sets the weighted average value as the pixel value of the pixel P2 in the composite high-frequency image GH1.

In the pixels P3, P8, and P10, three high-frequency tomographic images DH1 to DH3 including the linear structure are selected. Therefore, the combination unit 35 derives a weighted average value of the pixel values of the pixels P3, P8, and P10 in the high-frequency tomographic images DH1 to DH3 according to the feature amounts and sets the weighted average value as the pixel values of the pixels P3, P8, and P10 in the composite high-frequency image GH1.

In the pixel P4, three high-frequency tomographic images DH2 to DH4 are selected. Among them, two high-frequency tomographic images DH3 and DH4 are selected on the basis of the detection result of the calcification. Therefore, first, the combination unit 35 derives a weighted average value of the pixel values of the pixels P4 in the high-frequency tomographic images DH3 and DH4 according to the magnitudes of the variance values at the time of detecting the calcification in the pixel P4. Then, the combination unit 35 derives an added average value of the weighted average value of the pixel values of the pixels P4 in the high-frequency tomographic images DH3 and DH4 and the pixel value of the pixel P4 in the high-frequency tomographic image DH2 including the linear structure and sets the added average value as the pixel value of the pixel P4 in the composite high-frequency image GH1.

In the pixel P5, three high-frequency tomographic images DH2 to DH4 including the linear structure are selected. Therefore, the combination unit 35 derives a weighted average value of the pixel values of the pixels P5 in the high-frequency tomographic images DH2 to DH4 according to the feature amounts and sets the weighted average value as the pixel value of the pixel P5 in the composite high-frequency image GH1.

In the pixel P6, only the high-frequency tomographic image DH2 in which the calcification has been detected is selected. Therefore, the combination unit 35 uses the pixel value of the pixel P6 in the high-frequency tomographic image DH2 as the pixel value of the pixel P6 in the composite high-frequency image GH1.

In the pixels P7, P11 to P13, and P15, all of the high-frequency tomographic images DH1 to DH6 are selected. Therefore, the combination unit 35 derives an added average value of the pixel values of the pixels P7, P11 to P13, and P15 in the high-frequency tomographic images DH1 to DH6 and sets the added average value as the pixel values of the pixels P7, P11 to P13, and P15 in the composite high-frequency image GH1.

In the pixel P9, three high-frequency tomographic images DH4 to DH6 in which the calcification has been detected are selected. Therefore, the combination unit 35 derives a weighted average value of the pixel values of the pixels P9 in the high-frequency tomographic images DH4 to DH6 according to the magnitudes of the variance values calculated at the time of detecting the calcification and sets the weighted average value as the pixel value of the pixel P9 in the composite high-frequency image GH1.

In the pixel P14, three high-frequency tomographic images DH3 to DH5 in which the calcification has been detected are selected. Therefore, the combination unit 35 derives a weighted average value of the pixel values of the pixels P14 in the high-frequency tomographic images DH3 to DH5 according to the magnitudes of the variance values calculated at the time of detecting the calcification and sets the weighted average value as the pixel value of the pixel P14 in the composite high-frequency image GH1.

Figure 11:
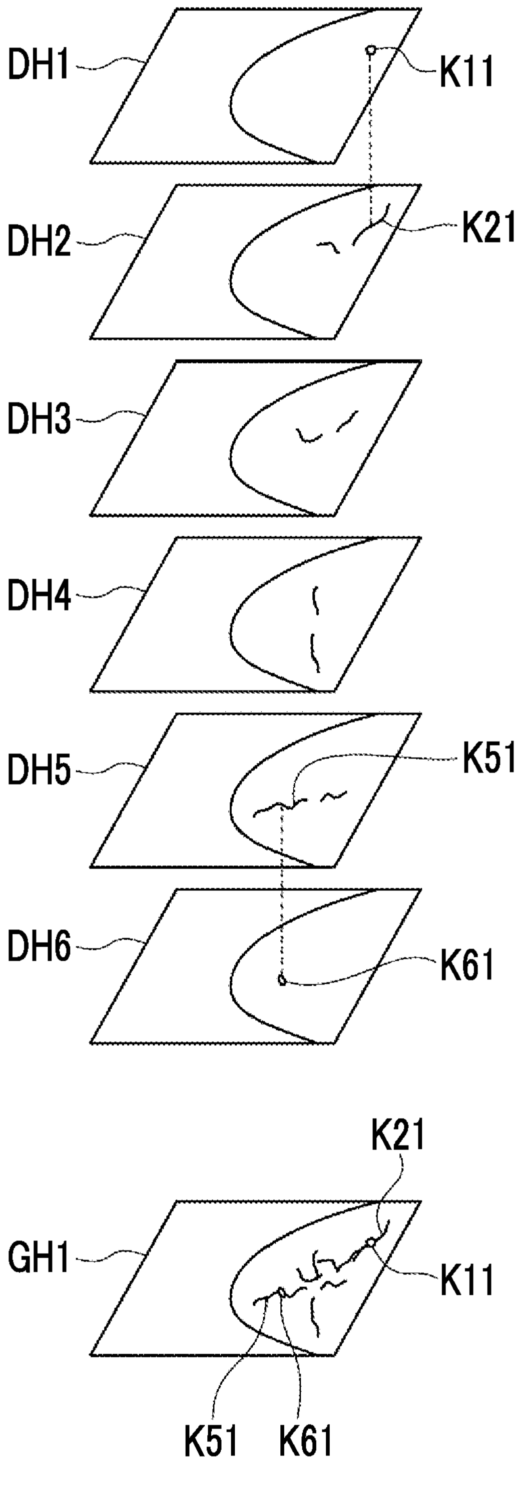
FIG. 11 is a diagram illustrating the generation of a composite high-frequency image.

FIG. 11 is a diagram illustrating the generation of a composite high-frequency image. In addition, the generation will be described using the six high-frequency tomographic images DH1 to DH6 in FIG. 11. As illustrated in FIG. 11, the high-frequency tomographic images DH1 to DH6 include linear structures and calcifications, and the linear structures and the calcifications included in the six high-frequency tomographic images DH1 to DH6 are combined and included in the composite high-frequency image GH1.

Here, the calcification K11 included in the tomographic image D1 is detected in the high-frequency tomographic image DH1. The calcification K11 overlaps the linear structure K21 included in the high-frequency tomographic image DH2. In this case, in the pixel corresponding to the calcification K11, the selection unit 34 selects the high-frequency tomographic image DH1 in which the calcification K11 has been detected, instead of the high-frequency tomographic image DH2 including the linear structure. Therefore, in the composite high-frequency image GH1, the linear structure K21 included in the high-frequency tomographic image DH2 is overwritten with the calcification K11 included in the high-frequency tomographic image DH1.

Further, the calcification K61 included in the tomographic image D6 is detected in the high-frequency tomographic image DH6. The calcification K61 overlaps the linear structure K51 included in the high-frequency tomographic image DH5. In this case, in the pixel corresponding to the calcification K61, the selection unit 34 selects the high-frequency tomographic image DH6 in which the calcification K61 has been detected, instead of the high-frequency tomographic image DH5 including the linear structure. Therefore, in the composite high-frequency image GH1, the linear structure K51 included in the high-frequency tomographic image DH5 is overwritten with the calcification K61 included in the high-frequency tomographic image DH6.

Meanwhile, the combination unit 35 derives an added average value of the pixel values of the corresponding pixels for all of the pixels of the low-frequency tomographic images DLj and sets the added average value as the pixel values of the composite low-frequency image GL1. In addition, the combination unit 35 may derive the composite low-frequency image GL1 using any method such as a method that calculates a variance value of each pixel for each of the low-frequency tomographic images DLj and derives a weighted average value corresponding to the magnitude of the variance value.

Figure 12:
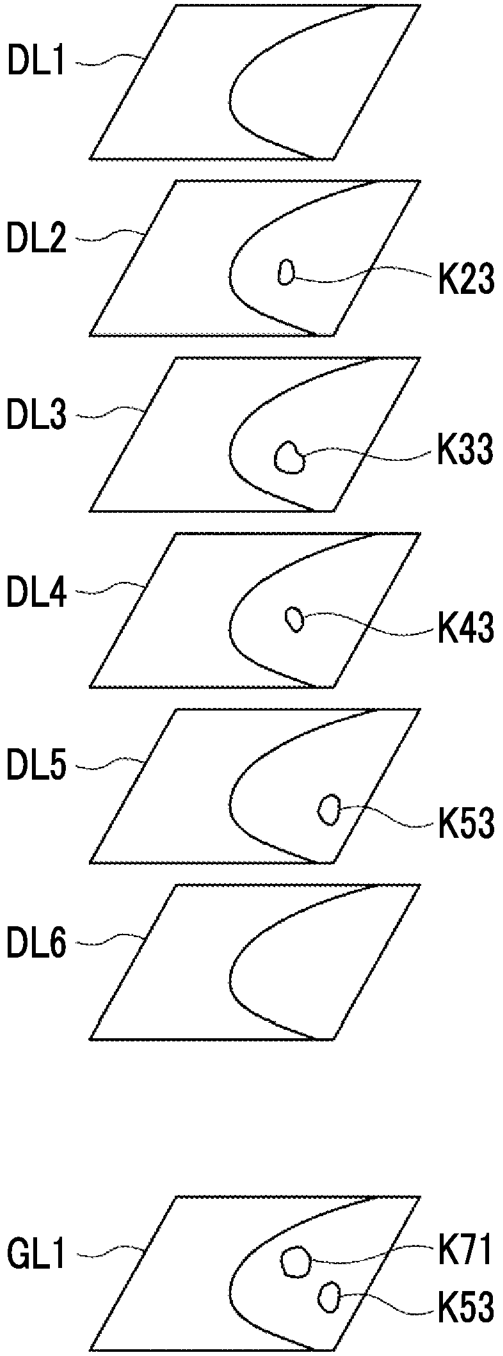
FIG. 12 is a diagram illustrating the generation of a composite low-frequency image.

FIG. 12 is a diagram illustrating the generation of a composite low-frequency image. In addition, in FIG. 12, the generation will be described using the six low-frequency tomographic images DL1 to DL6 illustrated in FIG. 8. As illustrated in FIG. 12, the low-frequency tomographic images DL2 to DL5 include low-frequency structures K23, K33, K43, and K53, such as tumors included in the breast M, respectively. Since the structures K23, K33, and K43 respectively included in the low-frequency tomographic images DL2 to DL4 overlap each other, the composite low-frequency GL1 includes a structure K71 which is an overlap of the structures K23, K33, and K43. Since the structure K53 included in the low-frequency tomographic image DL5 does not overlap any of the structures included in the other low-frequency tomographic images DL1 to DL4 and DL6, the structure K53 is included as it is in the composite low-frequency image GL1.

The combination unit 35 combines the composite high-frequency image GH1 and the composite low-frequency image GL1 to derive the composite two-dimensional image CG1. A method that corresponds to the derivation of the high-frequency linear structure by the linear structure image derivation unit 31 may be used as a combination method. For example, in a case in which the high-frequency tomographic images are derived by subtracting the enlarged low-frequency tomographic images DLj from the tomographic images Dj, the composite two-dimensional image CG1 is derived using, for example, the method disclosed in JP2018-029746A. Specifically, the composite two-dimensional image CG1 is derived by enlarging the low-frequency tomographic images DLj to have the same size as the original tomographic images Dj using an interpolation operation and adding the enlarged low-frequency tomographic images DLj and the composite high-frequency image GH1. In addition, the addition may be weighted addition. In this case, it is preferable that a weighting coefficient for the composite high-frequency image GH1 is larger than that for the composite low-frequency image GL1.

Figure 13:
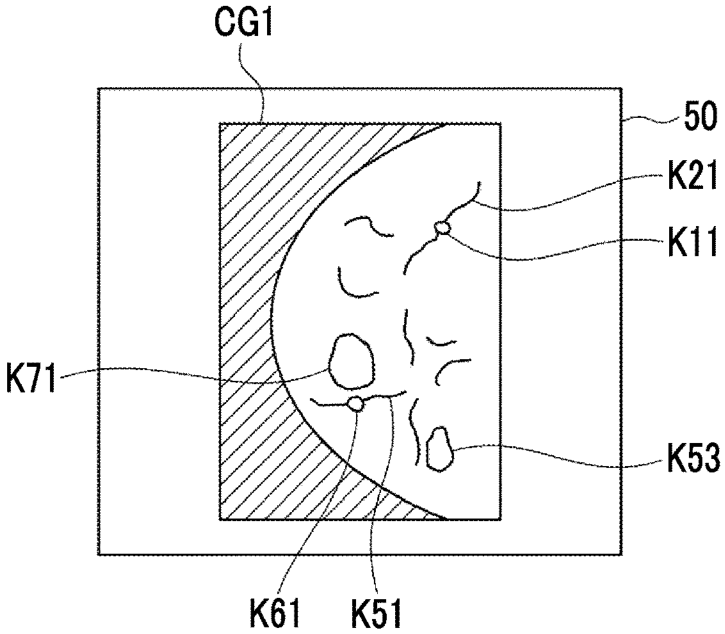
FIG. 13 is a diagram illustrating a composite two-dimensional image display screen in the first embodiment.

The display control unit 36 displays the composite two-dimensional image CG1 derived by the combination unit 35 on the display 24. FIG. 13 is a diagram illustrating a composite two-dimensional image display screen in the first embodiment. As illustrated in FIG. 13, the composite two-dimensional image CG1 is displayed on a display screen 50 of the display 24. In addition, the composite two-dimensional image CG1 illustrated in FIG. 13 is derived from the composite high-frequency image GH1 illustrated in FIG. 11 and the composite low-frequency image GL1 illustrated in FIG. 12. Further, in FIG. 13, all of the structures included in the tomographic images illustrated in FIG. 7 are not denoted by reference numerals. The composite two-dimensional image CG1 illustrated in FIG. 13 includes the linear structure, the calcification, and the low-frequency structure included in the tomographic images Dj. In particular, the calcification K11 included in the tomographic image D1 and the linear structure K21 included in the tomographic image D2 overlap each other. However, the linear structure K21 is replaced with the calcification K11 such that the calcification is easily seen. Further, the calcification K61 included in the tomographic image D6 and the linear structure K51 included in the tomographic image D5 overlap each other. However, the linear structure K51 is replaced with the calcification K61 such that the calcification is easily seen.

Figure 14:
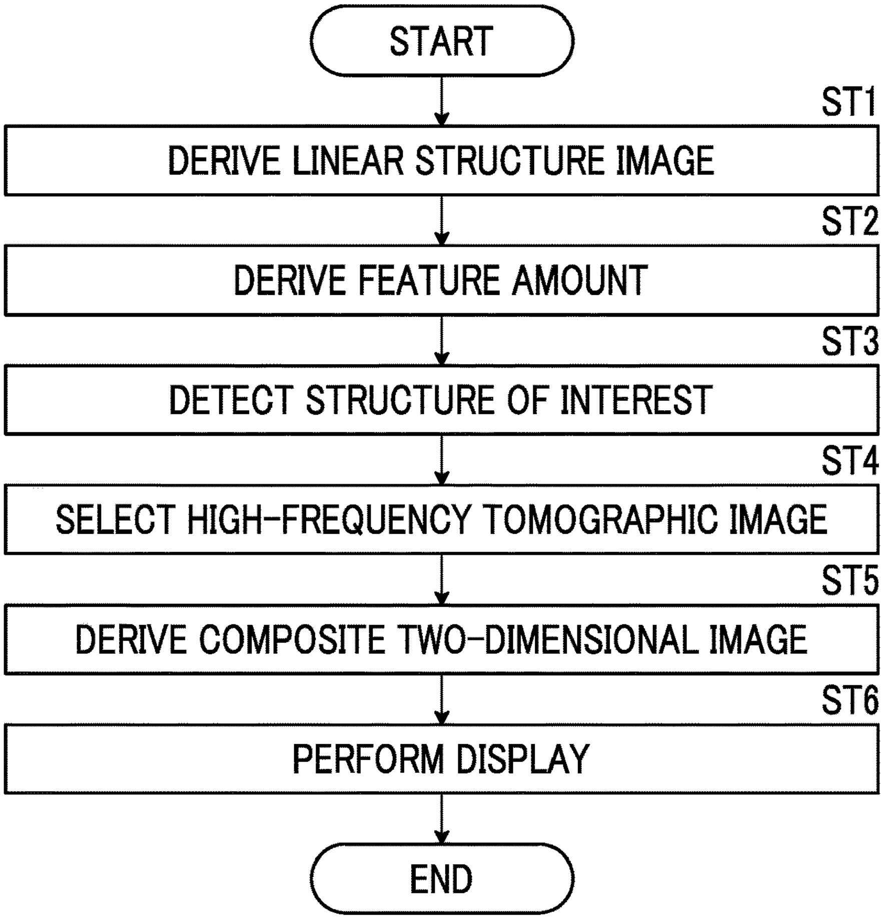
FIG. 14 is a flowchart illustrating a process performed in the first embodiment.

Next, a process performed in the first embodiment will be described. FIG. 14 is a flowchart illustrating the process performed in the first embodiment. In addition, it is assumed that a plurality of tomographic images Dj are acquired in advance and stored in the storage 23. The process is started in a case in which the input device 25 receives a process start instruction from an operator, and the linear structure image derivation unit 31 derives the linear structure images DSj from the plurality of tomographic images Dj (Step ST1). Then, the feature amount derivation unit 32 derives the feature amount indicating the features of the linear structure from each of the plurality of linear structure images DSj (Step ST2). In addition, the structure-of-interest detection unit 33 detects a calcification as the structure of interest from each of the plurality of tomographic images Dj or the high-frequency tomographic images DHj (Step ST3).

Then, the selection unit 34 selects the high-frequency tomographic image for each corresponding pixel in each of the high-frequency tomographic images DHj indicating the high-frequency components of the tomographic images Dj (Step ST4). That is, the selection unit 34 selects at least one high-frequency tomographic image including the linear structure or a predetermined high-frequency tomographic image for each corresponding pixel in each of the high-frequency tomographic images DHj on the basis of the feature amounts. In addition, in the corresponding pixel in the high-frequency tomographic images in which the calcification has been detected, the high-frequency tomographic images in which the calcification has been detected are selected instead of the high-frequency tomographic images including the linear structure or the predetermined high-frequency tomographic images.

Further, the combination unit 35 derives the composite two-dimensional image CG1 on the basis of the selected high-frequency tomographic images (Step ST5). Then, the display control unit 36 displays the composite two-dimensional image CG1 on the display 24 (Step ST6). Then, the process ends.

As described above, in the first embodiment, the linear structure images DSj are derived from the tomographic images Dj, and the feature amount indicating the features of the linear structure is derived from the linear structure images DSj. Then, at least one high-frequency tomographic image including the linear structure or a predetermined high-frequency tomographic image is selected for each corresponding pixel in each of the high-frequency tomographic images DHj on the basis of the feature amounts. Then, the composite two-dimensional image CG1 is derived on the basis of the selected high-frequency tomographic images. Here, in a case in which the linear structures included in the breast M overlap in the depth direction of the breast M (that is, the direction in which the tomographic images Dj are arranged), the feature amount becomes large. Therefore, the high-frequency tomographic images including the linear structure are selected. Therefore, the linear structure is clearly included in the composite two-dimensional image CG1, without blurring. Therefore, according to this embodiment, it is possible to easily see a fine structure included in the breast M in the composite two-dimensional image CG1.

In addition, in the first embodiment, the calcification is detected as the structure of interest from the tomographic images Dj or the high-frequency tomographic images DHj. In the pixel in which the calcification has been detected, the high-frequency tomographic images in which the calcification has been detected are selected, instead of the high-frequency tomographic images DHj including the linear structure or the predetermined high-frequency tomographic images DHj. Here, the calcification is an important structure for diagnosing breast cancer. Therefore, even in a case in which the calcification included in the breast M overlaps the linear structure in the depth direction of the breast M, the high-frequency tomographic image including the calcification is selected. Therefore, the calcification is clearly included in the composite two-dimensional image CG1 without being hidden by other structures in the breast M. Therefore, in the composite two-dimensional image CG1, the calcification included in the breast M can be easily seen.

In the first embodiment, the predetermined high-frequency tomographic images are selected in a case in which all of the feature amounts are 0 for each corresponding pixel in the high-frequency tomographic images DHj. However, the present disclosure is not limited thereto. In a case in which all of the feature amounts are less than a predetermined threshold value Th5 for each corresponding pixel in the high-frequency tomographic images DHj, the predetermined high-frequency tomographic images may be selected. In this case, in a case in which there is a pixel having a feature amount equal to or greater than the threshold value Th5, the high-frequency tomographic images DHj including the pixel are selected as the high-frequency tomographic images including the linear structure.

Figure 15:
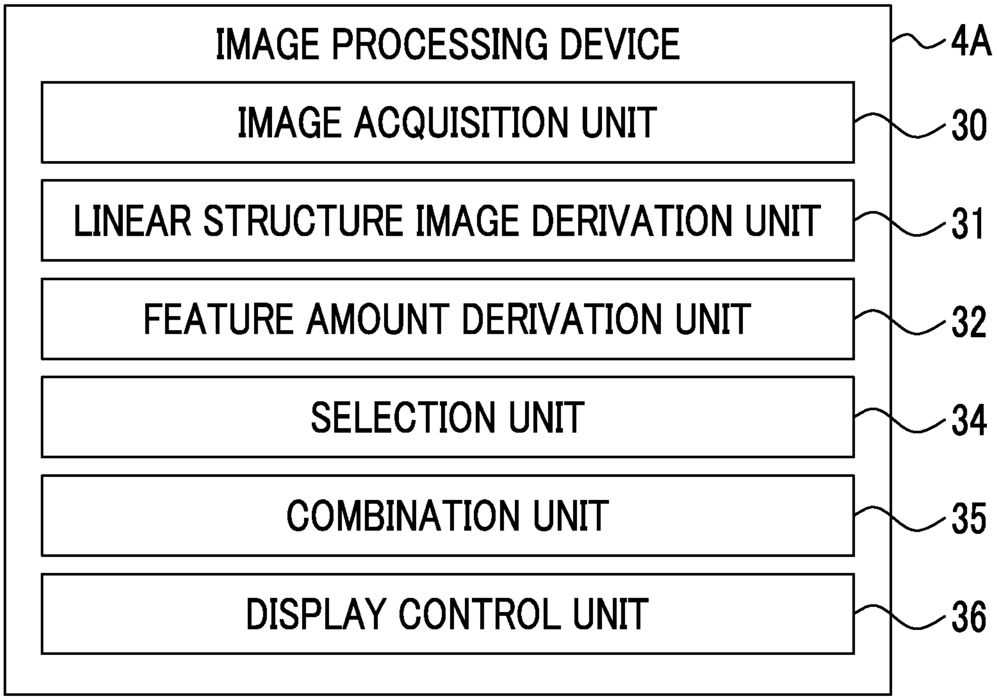
FIG. 15 is a diagram illustrating a functional configuration of an image processing device according to a second embodiment.

Next, a second embodiment of the present disclosure will be described. FIG. 15 is a diagram illustrating a functional configuration of an image processing device according to the second embodiment. In addition, in FIG. 15, the same components as those in FIG. 4 are denoted by the same reference numerals, and the detailed description thereof will not be repeated. An image processing device 4A according to the second embodiment differs from the image processing device 4 according to the first embodiment illustrated in FIG. 4 in that it does not include the structure-of-interest detection unit 33. In addition, in the second embodiment, the processes performed by the feature amount derivation unit 32, the selection unit 34, and the combination unit 35 are different from those in the first embodiment.

In the second embodiment, the feature amount derivation unit 32 converts the pixel value of each pixel of the linear structure images DSj to derive the feature amount. In the second embodiment, it is assumed that the pixel values of the linear structure images DSj have a larger value as brightness becomes higher (that is, closer to white). In addition, in the second embodiment, it is assumed that the average of the pixel values of the entire linear structure image is 0. That is, it is assumed that a pixel having high brightness (that is, white) has a positive value and a pixel having low brightness (that is, black) has a negative value. In the second embodiment, the pixel value of each pixel of the linear structure images DSj is converted, and an absolute value of the converted value is used as the feature amount. Specifically, the absolute value of a value obtained by adding a constant value to the pixel value of each pixel of the linear structure images DSj is used as the feature amount. Further, in a case in which the pixel value of each pixel of the linear structure images DSj is equal to or greater than 0, the absolute value of a value obtained by multiplying the pixel value of each pixel of the linear structure images DSj by a1 (a1>1) or a value obtained by adding a constant value to the pixel value may be used as the feature amount. Furthermore, in a case in which the pixel value of each pixel of the linear structure images DSj is equal to or less than 0, the absolute value of a value obtained by multiplying the pixel value of each pixel of the linear structure images DSj by a2 (a2<1) or a value obtained by adding a constant value to the pixel value may be used as the feature amount. Therefore, as a linear structure likeness becomes higher, the feature amount related to the linear structure images DSj becomes larger.

In addition, in a case in which each pixel of the linear structure images DSj has a smaller pixel value as the brightness becomes higher and the pixel value of each pixel of the linear structure images DSj is equal to or less than 0, the feature amount may be derived by multiplying the pixel value of each pixel of the linear structure images DSj by a3 (a3>1) or by subtracting a constant value from the pixel value. Further, in a case in which the average of the pixel values of the entire image is not 0, the feature amount may be calculated after the pixel values are converted such that the average of the pixel values is 0.

Here, in the first embodiment, the selection unit 34 selects the high-frequency tomographic images DHj. However, in the second embodiment, the selection unit 34 selects the tomographic images Dj used to generate the composite two-dimensional image on the basis of the feature amounts for each corresponding pixel in the tomographic images Dj, instead of the high-frequency tomographic images. In the second embodiment, at least one tomographic image including the linear structure or a predetermined tomographic image is selected for each corresponding pixel in each of the tomographic images Dj.

In addition, since the image processing device 4A according to the second embodiment does not include the structure-of-interest detection unit 33, the selection unit 34 according to the second embodiment selects the tomographic image without considering the calcification. That is, among the tomographic images Dj, a maximum of three tomographic images having a large feature amount in the linear structure images DSj are selected as the tomographic images including the linear structure for each corresponding pixel in the tomographic images Dj. Specifically, the selection unit 34 compares the feature amounts of the pixels corresponding to the pixels of interest in the linear structure images DSj for the corresponding pixel of interest in the tomographic images Dj. Then, the selection unit 34 specifies a maximum of three linear structure images DSj having a large feature amount.

For example, in a case in which the feature amounts of the corresponding pixel of interest in the six linear structure images DS1 to DS6 are 10, 30, 10, 40, 20, and 50, respectively, the selection unit 34 specifies the linear structure images DS2, DS4, and DS6 as the maximum of three linear structure images having a large feature amount for the pixel of interest. Then, the selection unit 34 selects the tomographic images D2, D4, and D6 corresponding to the specified linear structure images as the tomographic images including the linear structure for the pixel of interest. In addition, a maximum of three tomographic images having a feature amount equal to or greater than a predetermined threshold value Th6 may be selected as the tomographic images including the linear structure.

In addition, the number of selected tomographic images Dj including the linear structure is not limited to a maximum of three. For example, for each corresponding pixel in the tomographic images Dj, only one tomographic image having the maximum feature amount in the linear structure images DSj may be selected as the tomographic image including the linear structure. In addition, all of the tomographic images having a feature amount equal to or greater than a predetermined threshold value Th7 in the linear structure images DSj may be selected as the tomographic images including the linear structure. Further, in a case in which the number of tomographic images having a feature amount greater than 0 is less than three among the six tomographic images D1 to D6, the selection unit 34 may select one or two tomographic images having a feature amount greater than 0 as the tomographic images including the linear structure.

Furthermore, in a case in which all of the tomographic images Dj have a feature amount of 0 in the linear structure images DSj for each corresponding pixel in the tomographic images Dj, the selection unit 34 selects all of the tomographic images Dj as the predetermined tomographic images.

Figure 16:
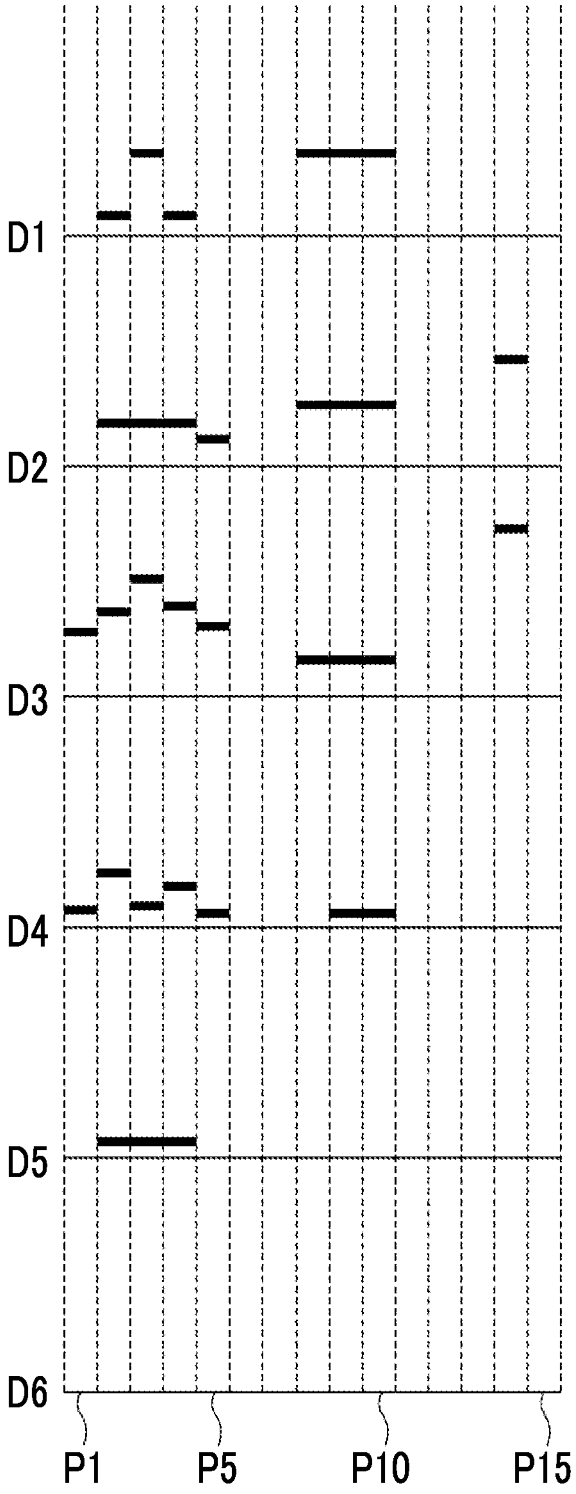
FIG. 16 is a diagram illustrating the selection of a tomographic image in the second embodiment.

FIG. 16 is a diagram illustrating the selection of the tomographic image using the feature amount in the second embodiment. In addition, in FIG. 16, the selection of the tomographic image from the six tomographic images D1 to D6 illustrated in FIG. 7 will be described. Further, in FIG. 16, the tomographic images D1 to D6 are schematically illustrated one-dimensionally. The illustration in FIG. 16 is the same as that in FIG. 10 except that the tomographic images D1 to D6 are used.

In the pixel P1, the feature amount of the linear structure is derived in the tomographic images D3 and D4. In this case, the selection unit 34 selects the two tomographic images D3 and D4 including the linear structure in the pixel P1.

In the pixel P2, the feature amount of the linear structure is derived in the tomographic images D1 to D5. Among the tomographic images D1 to D5, the tomographic images having the top three feature amounts are the tomographic images D2 to D4. Therefore, the selection unit 34 selects the three tomographic images D2 to D4 including the linear structure in the pixel P2.

In the pixel P3, the feature amount of the linear structure is derived in the tomographic images D1 to D5. Among the tomographic images D1 to D5, the tomographic images having the top three feature amounts are the tomographic images D1 to D3. Therefore, the selection unit 34 selects the three tomographic images D1 to D3 including the linear structure in the pixel P3.

In the pixel P4, the feature amount of the linear structure is derived in the tomographic images D1 to D5. Among the tomographic images D1 to D5, the tomographic images having the top three feature amounts are the tomographic images D2 to D4. Therefore, the selection unit 34 selects the three tomographic images D2 to D4 including the linear structure in the pixel P4.

Since the feature amount of the linear structure is derived in three tomographic images D2 to D4 in the pixel P5, the selection unit 34 selects the three tomographic images D2 to D4 including the linear structure in the pixel P5.

In the pixels P6 and P7, the feature amount of the linear structure is not derived in any of the tomographic images D1 to D6. Therefore, the selection unit 34 selects all of the tomographic images D1 to D6 as the predetermined tomographic images in the pixels P6 and P7.

In the pixel P8, the feature amount of the linear structure is derived from three tomographic images D1 to D3. Therefore, the selection unit 34 selects the three tomographic images D1 to D3 including the linear structure in the pixel P8.

In the pixels P9 and P10, the feature amount of the linear structure is derived in the tomographic images D1 to D4. Among the tomographic images D1 to D4, the tomographic images having the top three feature amounts are the tomographic images D1 to D3 in any of the pixels P9 and P10. Therefore, the selection unit 34 selects the three tomographic images D1 to D3 including the linear structure in the pixels P9 and P10.

In the pixels P11 to P13 and P15, the feature amount of the linear structure is not derived in any of the tomographic images D1 to D6. Therefore, the selection unit 34 selects all of the tomographic images D1 to D6 as the predetermined tomographic images in the pixels P11 to P13 and P15.

In the pixel P14, the feature amount of the linear structure is derived in the tomographic images D2 and D3. Therefore, the selection unit 34 selects the two tomographic images D2 and D3 including the linear structure in the pixel P14.

In the second embodiment, the combination unit 35 derives a composite two-dimensional image CG2 on the basis of the selected tomographic images.

In the pixel P1, the tomographic images D3 and D4 are selected. Therefore, the combination unit 35 derives a weighted average value of the pixel values of the pixels P1 in the tomographic images D3 and D4 according to the feature amounts derived for the corresponding linear structure images DS3 and DS4 and sets the weighted average value as the pixel value of the pixel P1 in the composite two-dimensional image CG2. In addition, a weighting coefficient for the weighted average is derived such that it becomes larger as the feature amount becomes larger. In addition, an added average value may be used instead of the weighted average value. This holds for the following description.

In the pixels P2, P4, and P5, the tomographic images D2 to D4 are selected. Therefore, the combination unit 35 derives a weighted average value of the pixel values of the pixels P2, P4, and P5 in the tomographic images D2 to D4 according to the feature amounts and sets the weighted average value as the pixel values of the pixels P2, P4, and P5 in the composite two-dimensional image CG2.

In the pixels P3 and P8 to P10, the tomographic images D1 to D3 are selected. Therefore, the combination unit 35 derives a weighted average value of the pixel values of the pixels P3 and P8 to P10 in the tomographic images D1 to D3 according to the feature amounts and sets the weighted average value as the pixel values of the pixels P3 and P8 to P10 in the composite two-dimensional image CG2.

In the pixels P6, P7, P11 to P13, and P15, all of the tomographic images D1 to D6 are selected. Therefore, the combination unit 35 derives an added average value of the pixel values of the pixels P6, P7, P11 to P13, and P15 in the tomographic images D1 to D6 and sets the added average value as the pixel values of the pixels P6, P7, P11 to P13, and P15 in the composite two-dimensional image CG2.

In the pixel P14, two tomographic images D2 and D3 are selected. Therefore, the combination unit 35 derives a weighted average value of the pixel values of the pixels P14 in the tomographic images D2 and D3 according to the feature amounts and sets the weighted average value as the pixel value of the pixel P14 in the composite two-dimensional image CG2.

Figure 17:
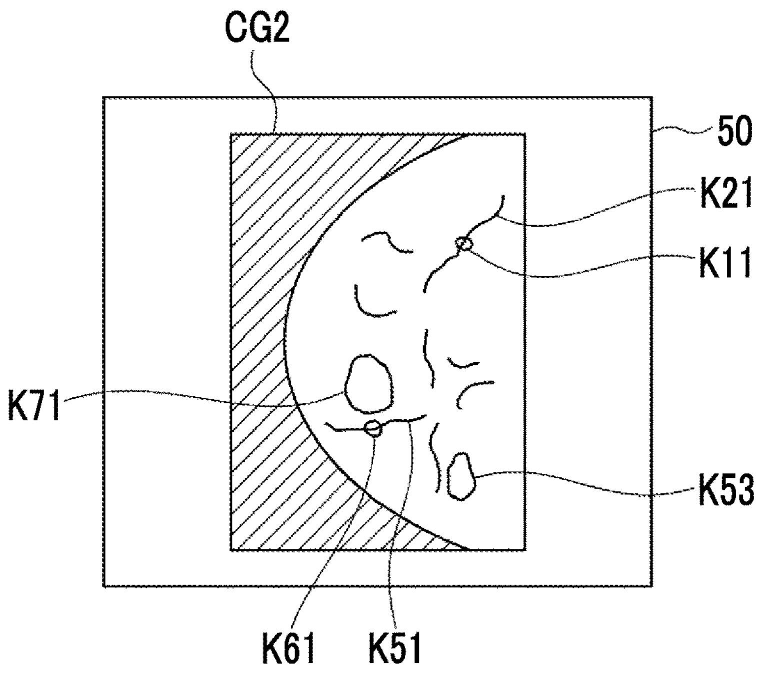
FIG. 17 is a diagram illustrating a composite two-dimensional image display screen in the second embodiment.

The display control unit 36 displays the composite two-dimensional image CG2 generated by the combination unit 35 on the display 24. FIG. 17 is a diagram illustrating a composite two-dimensional image display screen in the second embodiment. The composite two-dimensional image CG2 is displayed on a display screen 50 of the display 24 as illustrated in FIG. 17. In addition, the composite two-dimensional image CG2 illustrated in FIG. 17 is generated from the tomographic images Dj illustrated in FIG. 7. In addition, in FIG. 17, all of the structures included in the tomographic images illustrated in FIG. 7 are not denoted by reference numerals. The composite two-dimensional image CG2 illustrated in FIG. 17 includes the linear structure, the calcification, and the low-frequency structure included in the tomographic images Dj.

Here, in a case in which the composite two-dimensional image CG2 illustrated in FIG. 17 is compared with the composite two-dimensional image CG1 according to the first embodiment illustrated in FIG. 13, the calcification K11 included in the tomographic image D1 and the linear structure K21 included in the tomographic image D2 overlap each other in the composite two-dimensional image CG2. Further, the calcification K61 included in the tomographic image D6 and the linear structure K51 included in the tomographic image D5 overlap each other.

Figure 18:
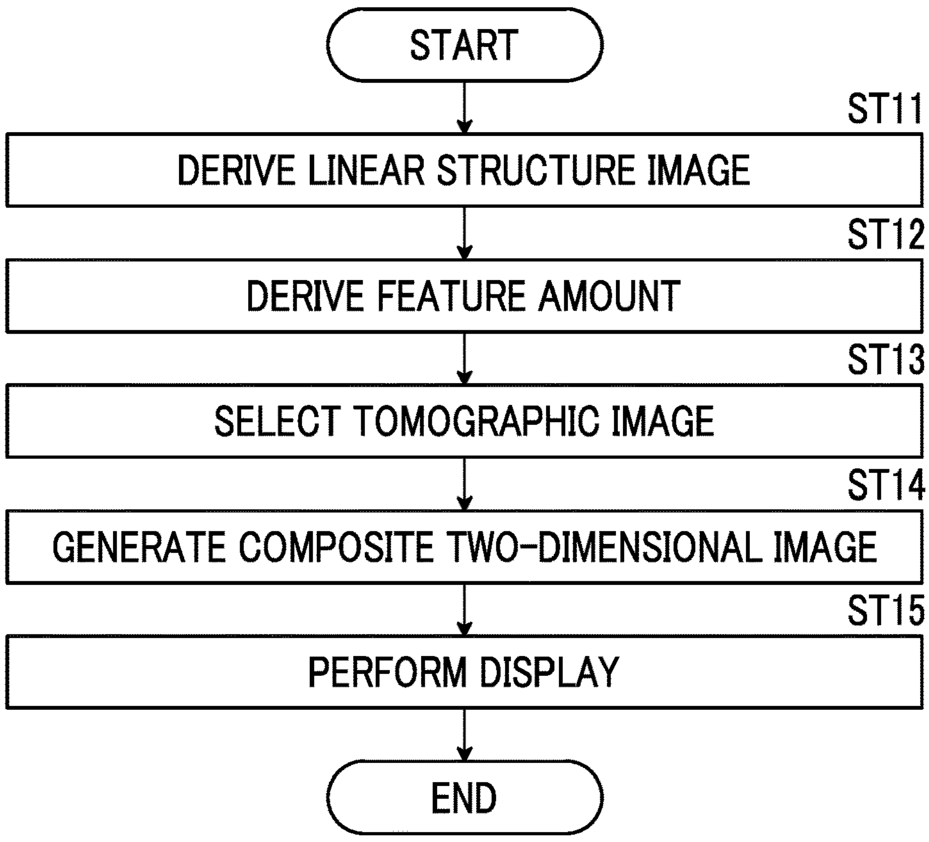
FIG. 18 is a flowchart illustrating a process performed in the second embodiment.

Next, a process performed in the second embodiment will be described. FIG. 18 is a flowchart illustrating the process performed in the second embodiment. In addition, it is assumed that a plurality of tomographic images Dj are acquired in advance and stored in the storage 23. The process is started in a case in which the input device 25 receives a process start instruction from the operator, and the linear structure image derivation unit 31 derives the linear structure images DSj from the plurality of tomographic images Dj (Step ST11). Then, the feature amount derivation unit 32 derives the feature amount indicating the features of the linear structure from each of the plurality of linear structure images DSj (Step ST12).

Then, the selection unit 34 selects the tomographic image on the basis of the feature amount for each corresponding pixel in each of the tomographic images Dj (Step ST13). That is, the selection unit 34 selects at least one tomographic image including the linear structure or a predetermined tomographic image for each corresponding pixel in each of the tomographic images Dj on the basis of the feature amount.

Further, the combination unit 35 derives the composite two-dimensional image CG2 on the basis of the selected tomographic images (Step ST14). Then, the display control unit 36 displays the composite two-dimensional image CG2 on the display 24 (Step ST15). Then, the process ends.

In addition, the image processing device 4A according to the second embodiment may be provided with the structure-of-interest detection unit 33 as in the first embodiment. In this case, the selection unit 34 selects the tomographic images Dj used to generate the composite two-dimensional image CG2 on the basis of the feature amounts derived by the feature amount derivation unit 32 and the calcification detected by the structure-of-interest detection unit 33 for each corresponding pixel in the tomographic images Dj.

Further, in the second embodiment, the selection unit 34 selects the tomographic images Dj, and the combination unit 35 combines the tomographic images Dj to derive the composite two-dimensional image CG2. However, the present disclosure is not limited thereto. As in the first embodiment, the selection unit 34 may select the high-frequency tomographic images DHj used to generate the composite two-dimensional image on the basis of the feature amounts derived by the feature amount derivation unit 32. In this case, as in the first embodiment, the combination unit 35 may derive a composite high-frequency image (represented by GH2) and a composite low-frequency image (represented by GL2) and combine the composite high-frequency image GH2 and the composite low-frequency image GL2 to derive the composite two-dimensional image CG2.

Next, a third embodiment of the present disclosure will be described. In addition, a functional configuration of an image processing device according to the third embodiment is the same as the functional configuration of the image processing device 4 according to the first embodiment except only the process to be performed. Therefore, the detailed description of the device will not be repeated here. The third embodiment differs from the first embodiment in the processes performed by the linear structure image derivation unit 31, the feature amount derivation unit 32, the selection unit 34, and the combination unit 35.

In the third embodiment, the linear structure image derivation unit 31 performs a filtering process using a high-pass filter on the tomographic images Dj to derive the high-frequency tomographic images DHj indicating the high-frequency components of the tomographic images Dj. In addition, the linear structure image derivation unit 31 performs a filtering process using a low-pass filter on the tomographic images Dj to derive the low-frequency tomographic images DLj indicating the low-frequency components of the tomographic images Dj. Then, the linear structure image derivation unit 31 highlights the high-frequency components of the tomographic images Dj on the basis of the high-frequency tomographic images DHj. Specifically, the high-frequency components of the tomographic images Dj are highlighted by multiplying the pixel values of the pixels of the tomographic images Dj, which correspond to the pixels having pixel values equal to or greater than a threshold value in the high-frequency tomographic images DHj, by a4 ($a4>1$) or by adding a constant value to the pixel values. In addition, the linear structure image derivation unit 31 suppresses the low-frequency components of the tomographic images Dj, in which the high-frequency components have been highlighted, on the basis of the low-frequency tomographic images DLj. Specifically, the low-frequency components of the tomographic images Dj, in which the high-frequency components have been highlighted, are suppressed by multiplying the pixel values of the pixels of the tomographic images Dj, which correspond to the pixels having pixel values equal to or greater than a threshold value in the low-frequency tomographic images DLj, by a5 ($a5<1$) or by subtracting a constant value from the pixel values.

Further, the linear structure image derivation unit 31 applies a directional filter to the tomographic images Dj in the direction in which the pixels of the tomographic images Dj, in which the high-frequency components have been highlighted and the low-frequency components have been suppressed, are connected to extract the high-frequency linear structures, thereby deriving the linear structure images DSj. In the third embodiment, in a case in which the linear structure images DSj are derived, only the highlighting of the high-frequency components of the tomographic images Dj may be performed. In this case, the derivation of the low-frequency tomographic images DLj is unnecessary. In addition, in the third embodiment, in a case in which the linear structure images DSj are derived, only the suppression of the low-frequency components of the tomographic images Dj may be performed. In this case, the derivation of the high-frequency tomographic images DHj is unnecessary.

In the third embodiment, the selection unit 34 selects the tomographic images Dj used to generate the composite two-dimensional image on the basis of the feature amounts derived by the feature amount derivation unit 32 and the calcification detected by the structure-of-interest detection unit 33 for each corresponding pixel in the tomographic images Dj. In this case, first, the selection unit 34 selects the tomographic images Dj on the basis of the calcification detected by the structure-of-interest detection unit 33. That is, in a case in which the calcification is detected in the corresponding pixels in the tomographic images Dj, in the third embodiment, first, the selection unit 34 selects the tomographic images Dj in which the calcification has been detected. In this case, as in the first embodiment, a predetermined number (for example, a maximum of 3) of tomographic images Dj, in which a variance value at the time of detecting the calcification is equal to or greater than a threshold value Th8, are selected. In addition, all of the tomographic images Dj, in which the calcification has been detected, may be selected. Further, one tomographic image Dj having the maximum variance value at the time of detecting the calcification may be selected.

For example, in a case in which the calcification is detected in the tomographic images D2 and D3 for the corresponding pixels of interest in the six tomographic images D1 to D6, the selection unit 34 selects the tomographic images D2 and D3 as the tomographic images used to generate the composite two-dimensional image for the pixel of interest. In addition, in a case in which the calcification is detected in the tomographic images, whose number is greater than a predetermined number, for the pixel of interest, the tomographic images having a predetermined number of high-ranking variance values at the time of detecting the calcification may be selected.

Further, in the third embodiment, for the pixels in which the calcification has not been detected, the selection unit 34 selects at least one tomographic image including the linear structure or a predetermined tomographic image on the basis of the feature amount for each corresponding pixel in the tomographic images Dj. The selection of the at least one tomographic image including the linear structure or the predetermined tomographic image is performed in the same manner as that in the second embodiment.

Figure 19:
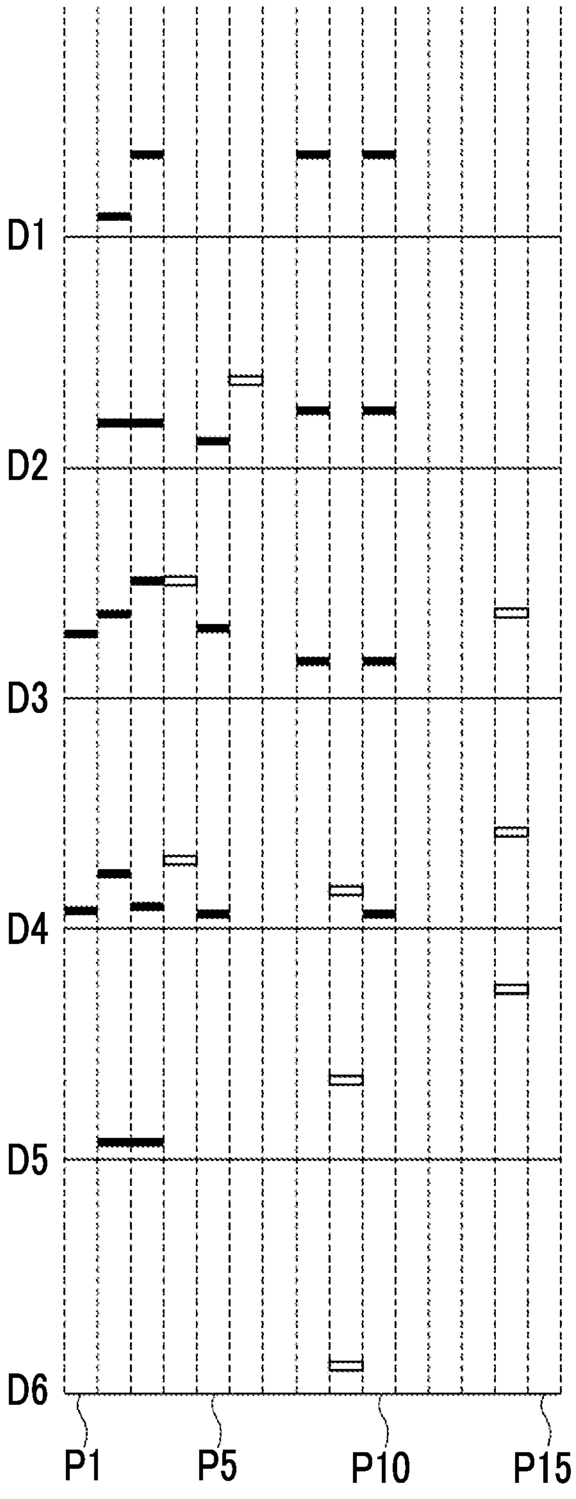
FIG. 19 is a diagram illustrating the selection of a tomographic image in a third embodiment.

FIG. 19 is a diagram illustrating the selection of the tomographic image in the third embodiment. In addition, in FIG. 19, the selection of the tomographic image from the six tomographic images D1 to D6 illustrated in FIG. 7 will be described. Further, in FIG. 19, the tomographic images D1 to D6 are schematically illustrated one-dimensionally. Furthermore, the illustration in FIG. 19 is the same as that in FIG. 10 except that the tomographic images D1 to D6 are used.

The calcification is detected in the pixels P4, P6, P9, and P14 as illustrated in FIG. 19. In the pixel P4, the calcification is detected in the tomographic images D3 and D4. Therefore, the selection unit 34 selects the tomographic images D3 and D4 in the pixel P4. In the pixel P6, the calcification is detected in the tomographic image D2. Therefore, the selection unit 34 selects the tomographic image D2 in the pixel P6. In the pixel P9, the calcification is detected in the tomographic images D4 to D6. Therefore, the selection unit 34 selects the tomographic images D4 to D6 in the pixel P9. In the pixel P14, the calcification is detected in the tomographic images D3 to D5. Therefore, the selection unit 34 selects the tomographic images D3 to D5 in the pixel P14.

Further, in the pixels P1 to P3, P5, P7, P8, P10 to P13, and P15 in which the calcification has not been detected, the selection unit 34 selects the tomographic images Dj on the basis of the feature amounts derived by the feature amount derivation unit 32 for each corresponding pixel in the tomographic images Dj.

Next, the pixels P1 to P3, P5, P7, P8, P10 to P13, and P15 in which the calcification has not been detected will be described.

In the pixel P1, the feature amount of the linear structure is derived in the tomographic images D3 and D4. In this case, the selection unit 34 selects the two tomographic images D3 and D4 including the linear structure in the pixel P1.

In the pixel P2, the feature amount of the linear structure is derived in the tomographic images D1 to D5. Among the tomographic images D1 to D5, the tomographic images having the top three feature amounts are the tomographic images D2 to D4. Therefore, the selection unit 34 selects the three tomographic images D2 to D4 including the linear structure in the pixel P2.

In the pixel P3, the feature amount of the linear structure is derived in the tomographic images D1 to D5. Among the tomographic images D1 to D5, the tomographic images having the top three feature amounts are the tomographic images D1 to D3. Therefore, the selection unit 34 selects the three tomographic images D1 to D3 including the linear structure in the pixel P3.

In the pixel P5, the feature amount of the linear structure is derived in three tomographic images D2 to D4. Therefore, the selection unit 34 selects the three tomographic images D2 to D4 including the linear structure in the pixel P5.

In the pixel P7, the feature amount of the linear structure is not derived in any of the tomographic images D1 to D6. Therefore, the selection unit 34 selects all of the tomographic images D1 to D6 as the predetermined tomographic images in the pixel P7.

In the pixel P8, the feature amount of the linear structure is derived from three tomographic images D1 to D3. Therefore, the selection unit 34 selects the three tomographic images D1 to D3 including the linear structure in the pixel P8.

In the pixel P10, the feature amount of the linear structure is derived in the tomographic images D1 to D4. Among the tomographic images D1 to D4, the tomographic images having the top three feature amounts are the tomographic images D1 to D3. Therefore, the selection unit 34 selects the three tomographic images D1 to D3 including the linear structure in the pixel P10.

In the pixels P11 to P13 and P15, the feature amount of the linear structure is not derived in any of the tomographic images D1 to D6. Therefore, the selection unit 34 selects all of the tomographic images D1 to D6 as the predetermined tomographic images in the pixels P11 to P13 and P15.

In the third embodiment, the combination unit 35 derives a composite two-dimensional image CG3 on the basis of the selected tomographic images in a region of the linear structure and the calcification and derives the composite two-dimensional image CG3 on the basis of the predetermined tomographic images in a region other than the linear structure and the calcification.

In the pixel P1, the tomographic images D3 and D4 are selected. Therefore, the combination unit 35 derives a weighted average value of the pixel values of the pixels P1 in the tomographic images D3 and D4 according to the feature amounts derived for the corresponding linear structure images DS3 and DS4 and sets the weighted average value as the pixel value of the pixel P1 in the composite two-dimensional image CG3. In addition, a weighting coefficient for the weighted average is derived such that it becomes larger as the feature amount becomes larger. In addition, an added average value may be used instead of the weighted average value. This holds for the following description.

In the pixels P2 and P5, the tomographic images D2 to D4 are selected. Therefore, the combination unit 35 derives a weighted average value of the pixel values of the pixels P2 and P5 in the tomographic images D2 to D4 according to the feature amounts and sets the weighted average value as the pixel values of the pixels P2 and P5 in the composite two-dimensional image CG3.

In the pixels P3, P8, and P10, the tomographic images D1 to D3 are selected. Therefore, the combination unit 35 derives a weighted average value of the pixel values of the pixels P3, P8, and P10 in the tomographic images D1 to D3 according to the feature amounts and sets the weighted average value as the pixel values of the pixels P3, P8, and P10 in the composite two-dimensional image CG3.

In the pixel P4, the tomographic images D3 and D4 are selected. Therefore, the combination unit 35 derives a weighted average value of the pixel values of the pixels P4 in the tomographic images D3 and D4 according to the variance value used at the time of detecting the calcification and sets the weighted average values as the pixel value of the pixel P4 in the composite two-dimensional image CG3.

In the pixel P6, the tomographic image D2 is selected. Therefore, the combination unit 35 sets the pixel value of the pixel P6 in the tomographic image D2 as the pixel value of the pixel P6 in the composite two-dimensional image CG3.

In the pixels P7, P11 to P13, and P15, all of the tomographic images D1 to D6 are selected. Therefore, the combination unit 35 derives an added average value of the pixel values of the pixel values of the pixels P7, P11 to P13, and P15 in the tomographic images D1 to D6 and sets the added average value as the pixel values of the pixels P7, P11 to P13, and P15 in the composite two-dimensional image CG3.

In the pixel P9, the tomographic images D4 to D6 are selected. Therefore, the combination unit 35 derives a weighted average value of the pixel values of the pixels P9 in the tomographic images D4 to D6 according to the variance values used at the time of detecting the calcification and sets the weighted average value as the pixel value of the pixel P9 in the composite two-dimensional image CG3.

In the pixel P14, the tomographic images D3 to D5 are selected. Therefore, the combination unit 35 derives a weighted average value of the pixel values of the pixels P14 in the tomographic images D3 to D6 according to the variance value used at the time of detecting the calcification and sets the weighted average value as the pixel value of the pixel P14 in the composite two-dimensional image CG3.

In addition, the composite two-dimensional image CG3 derived in the third embodiment is substantially the same as the composite two-dimensional image CG1 derived in the first embodiment.

Figure 20:
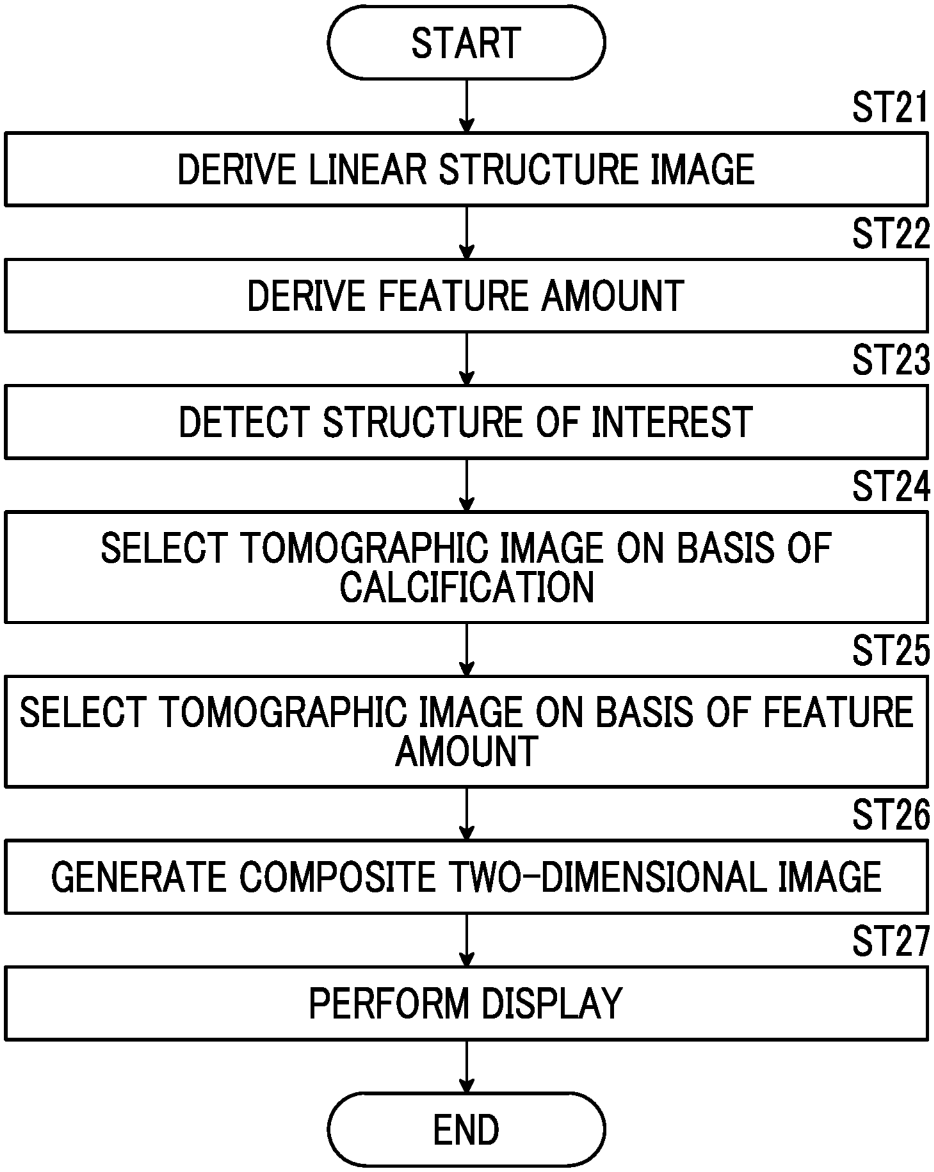
FIG. 20 is a flowchart illustrating a process performed in the third embodiment.

Next, a process performed in the third embodiment will be described. FIG. 20 is a flowchart illustrating the process performed in the third embodiment. In addition, it is assumed that a plurality of tomographic images Dj are acquired in advance and stored in the storage 23. The process is started in a case in which the input device 25 receives a process start instruction from the operator, and the linear structure image derivation unit 31 derives the linear structure images DSj from a plurality of tomographic images Dj (Step ST21). Then, the feature amount derivation unit 32 derives the feature amount indicating the features of the linear structure from each of the plurality of linear structure images DSj (Step ST22). In addition, the structure-of-interest detection unit 33 detects the calcification as the structure of interest from each of the plurality of tomographic images Dj (Step ST23).

Then, the selection unit 34 selects at least one tomographic image including the calcification on the basis of the detected calcification for each corresponding pixel in each of the tomographic images Dj (Step ST24). In addition, the selection unit 34 selects the tomographic image on the basis of the feature amount for each corresponding pixel in each of the tomographic images Dj (Step ST25). That is, the selection unit 34 selects at least one tomographic image including the linear structure or a predetermined tomographic image for each corresponding pixel in each of the tomographic images Dj on the basis of the feature amount.

Further, the combination unit 35 derives the composite two-dimensional image CG3 on the basis of the selected tomographic images (Step ST26). Then, the display control unit 36 displays the composite two-dimensional image CG3 on the display 24 (Step ST27). Then, the process ends.

In addition, in the first embodiment, the structure-of-interest detection unit 33 detects the calcification as the structure of interest from the tomographic images Dj, and the tomographic image is selected also on the basis of the calcification. However, the present disclosure is not limited thereto. In the first embodiment, the structure-of-interest detection unit 33 may not be provided, and the high-frequency tomographic images DHj may be selected on the basis of only the feature amounts.

In addition, in the first embodiment, the feature amount derivation unit 32 may derive the feature amount as in the second or third embodiment.

In addition, in the first and second embodiments, the linear structure image derivation unit 31 may derive the linear structure image as in the third embodiment.

Further, in the first embodiment, the composite high-frequency image may be derived in advance by calculating, for example, the weighted average value of the pixel values of the corresponding pixels in the high-frequency tomographic images DHj. The composite high-frequency image derived in advance is referred to as a pre-composite high-frequency image. In this case, the selection unit 34 selects only the high-frequency tomographic image including the linear structure or the high-frequency tomographic image in which the calcification has been detected. Further, in this case, the combination unit 35 derives the composite high-frequency image GH1 using the pre-composite high-frequency image.

Specifically, among the pixels of the high-frequency tomographic images DHj, for the pixel for which the high-frequency tomographic image including the linear structure has been selected and the pixel for which the high-frequency tomographic image in which the calcification has been detected has been selected, the pixel values of the composite high-frequency image GH1 are derived using the high-frequency tomographic image including the linear structure and the high-frequency tomographic image in which the calcification has been detected. On the other hand, for the pixel for which the high-frequency tomographic image including the linear structure or the high-frequency tomographic image in which the calcification has been detected is not selected, the pixel value of the corresponding pixel in the pre-composite high-frequency image is used as the pixel value of the composite high-frequency image GH1. In addition, the pixel values of the composite high-frequency image GH1 may be derived using the high-frequency tomographic image including the linear structure and the high-frequency tomographic image in which the calcification has been detected, and the derived pixel values may be added to the pre-composite high-frequency image to derive the composite high-frequency image GH1.

Further, in the second and third embodiments, the composite two-dimensional image may be derived in advance by calculating, for example, a weighted average value of the pixel values of the corresponding pixels in the tomographic images Dj. The composite two-dimensional image derived in advance is referred to as a pre-composite image. In this case, the selection unit 34 selects only the tomographic image including the linear structure or the tomographic image in which the calcification has been detected. Further, in this case, the combination unit 35 derives the composite two-dimensional images CG2 and CG3 using the pre-composite image.

Specifically, among the pixels of the tomographic images Dj, for the pixels for which the tomographic image including the linear structure and the tomographic image in which the calcification has been detected are selected, the pixel values of the composite two-dimensional images CG2 and CG3 are derived using the tomographic images including the linear structure and the tomographic images in which the calcification has been detected. On the other hand, for the pixel for which the tomographic image including the linear structure or the tomographic image in which the calcification has been detected is not selected, the pixel value of the corresponding pixel in the pre-composite image is used as the pixel value of the composite two-dimensional images CG2 and CG3. In addition, the pixel values of the composite two-dimensional images CG2 and CG3 may be derived using the tomographic images including the linear structure and the tomographic images in which the calcification has been detected, and the derived pixel values may be added to the pre-composite image to derive the composite two-dimensional images CG2 and CG3.

Further, the radiation in each of the above-described embodiments is not particularly limited. For example, α-rays or γ-rays can be applied in addition to the X-rays.

Furthermore, in each of the above-described embodiments, for example, the following various processors can be used as a hardware structure of processing units performing various processes, such as the image acquisition unit 30, the linear structure image derivation unit 31, the feature amount derivation unit 32, the structure-of-interest detection unit 33, the selection unit 34, the combination unit 35, and the display control unit 36. The various processors include, for example, a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

What is claimed is:

1. An image processing device comprising:

at least one processor configured to generate a plurality of tomographic images indicating tomographic planes of an object by reconstructing a plurality of projection images;

to derive a linear structure image indicating a high-frequency linear structure from each of the plurality of tomographic images;

to derive a feature amount indicating features of the linear structure from the linear structure image, wherein the feature amount includes, for each pixel position, a variance value of pixel values within a region of interest in the linear structure image;

to detect a structure of interest from the tomographic image or a high-frequency tomographic image;

to select at least one tomographic image or the high-frequency tomographic image on the basis of the feature amount and the detected structure of interest for each corresponding pixel in each of the tomographic images or the high-frequency tomographic images, by selecting, for each pixel position, up to three tomographic images or high-frequency tomographic images corresponding to mutually different tomographic planes, having three highest feature amounts at the pixel position, wherein, when the structure of interest is detected at the pixel position in at least one tomographic image or high-frequency tomographic image, the selecting includes selecting, for the pixel position, the tomographic image or high-frequency tomographic image in which the structure of interest is detected instead of an image from among the up to three tomographic images or high-frequency tomographic images having the three highest feature amounts at the pixel position;

to derive a composite two-dimensional image on the basis of the selected tomographic images or high-frequency tomographic images, wherein the composite two-dimensional image is a diagnostic display image in which obscuration of the structure of interest by the linear structure is reduced by using, at pixel positions where the structure of interest is detected, pixel values from the tomographic image or high-frequency tomographic image in which the structure of interest is detected; and to output the diagnostic display image to a display device to assist a user in detecting the structure of interest, wherein the high-frequency tomographic images indicate high-frequency components of the tomographic images, and wherein the selected tomographic images or high-frequency tomographic images correspond to mutually different tomographic planes.

2. The image processing device according to claim 1, wherein the processor is configured to select the at least one tomographic image or high-frequency tomographic image including the linear structure and to derive the composite two-dimensional image on the basis of a pre-composite image generated in advance on the basis of the tomographic images or the high-frequency tomographic images and the selected tomographic images or high-frequency tomographic images.

3. The image processing device according to claim 2, wherein the object is a breast, and the linear structure is a mammary gland and a spicula.

4. The image processing device according to claim 2, wherein the processor is configured to convert a pixel value of the linear structure image to derive the feature amount.

5. The image processing device according to claim 2, wherein the processor is configured to select the tomographic image or the high-frequency tomographic image that includes the linear structure having the feature amount equal to or greater than a predetermined threshold value.

6. The image processing device according to claim 1, wherein the object is a breast, and the structure of interest is a calcification.

7. The image processing device according to claim 1, wherein the object is a breast, and the linear structure is a mammary gland and a spicula.

8. The image processing device according to claim 1, wherein the processor is configured to convert a pixel value of the linear structure image to derive the feature amount.

9. The image processing device according to claim 1, wherein the processor is configured to select the tomographic image or the high-frequency tomographic image that includes the linear structure having the feature amount equal to or greater than a predetermined threshold value.

10. The image processing device according to claim 1, wherein the processor is configured to derive a composite two-dimensional image on the basis of the selected tomographic images or high-frequency tomographic images, and low-frequency tomographic images indicating low-frequency components of the tomographic images.

11. An image processing method comprising:

generating a plurality of tomographic images indicating tomographic planes of an object by reconstructing a plurality of projection images;

deriving a linear structure image indicating a high-frequency linear structure from each of the plurality of tomographic images;

deriving a feature amount indicating features of the linear structure from the linear structure image, wherein the feature amount includes, for each pixel position, a variance value of pixel values within a region of interest in the linear structure image;

detecting a structure of interest from the tomographic image or a high-frequency tomographic image;

selecting at least one tomographic image or the high-frequency tomographic image on the basis of the feature amount and the detected structure of interest for each corresponding pixel in each of the tomographic images or the high-frequency tomographic images, by selecting, for each pixel position, up to three tomographic images or high-frequency tomographic images corresponding to mutually different tomographic planes, having three highest feature amounts at the pixel position, wherein, when the structure of interest is detected at the pixel position in at least one tomographic image or high-frequency tomographic image, the selecting includes selecting, for the pixel position, the tomographic image or high-frequency tomographic image in which the structure of interest is detected instead of an image from among the up to three tomographic images or high-frequency tomographic images having the three highest feature amounts at the pixel position;

deriving a composite two-dimensional image on the basis of the selected tomographic images or high-frequency tomographic images, wherein the composite two-dimensional image is a diagnostic display image in which obscuration of the structure of interest by the linear structure is reduced by using, at pixel positions where the structure of interest is detected, pixel values from the tomographic image or high-frequency tomographic image in which the structure of interest is detected; and outputting the diagnostic display image to a display device to assist a user in detecting the structure of interest, wherein the high-frequency tomographic images indicate high-frequency components of the tomographic images, and wherein the selected tomographic images or high-frequency tomographic images correspond to mutually different tomographic planes.

12. A non-transitory computer-readable storage medium storing an image processing program that causes a computer to execute:

a procedure of generating a plurality of tomographic images indicating tomographic planes of an object by reconstructing a plurality of projection images;

a procedure of deriving a linear structure image indicating a high-frequency linear structure from each of the plurality of tomographic images;

a procedure of deriving a feature amount indicating features of the linear structure from the linear structure image, wherein the feature amount includes, for each pixel position, a variance value of pixel values within a region of interest in the linear structure image;

a procedure of detecting a structure of interest from the tomographic image or a high-frequency tomographic image;

a procedure of selecting at least one tomographic image or the high-frequency tomographic image on the basis of the feature amount and the detected structure of interest for each corresponding pixel in each of the tomographic images or the high-frequency tomographic images, by selecting, for each pixel position, up to three tomographic images or high-frequency tomographic images corresponding to mutually different tomographic planes, having three highest feature amounts at the pixel position, wherein, when the structure of interest is detected at the pixel position in at least one tomographic image or high-frequency tomographic image, the selecting includes selecting, for the pixel position, the tomographic image or high-frequency tomographic image in which the structure of interest is detected instead of an image from among the up to three tomographic images or high-frequency tomographic images having the three highest feature amounts at the pixel position;

a procedure of deriving a composite two-dimensional image on the basis of the selected tomographic images or high-frequency tomographic images, wherein the composite two-dimensional image is a diagnostic display image in which obscuration of the structure of interest by the linear structure is reduced by using, at pixel positions where the structure of interest is detected, pixel values from the tomographic image or high-frequency tomographic image in which the structure of interest is detected; and a procedure of outputting the diagnostic display image to a display device to assist a user in detecting the structure of interest, wherein the high-frequency tomographic images indicate high-frequency components of the tomographic images, and wherein the selected tomographic images or high-frequency tomographic images correspond to mutually different tomographic planes.

* * * * *